(12) United States Patent
Bornzin et al.

(10) Patent No.: US 12,036,404 B2
(45) Date of Patent: Jul. 16, 2024

(54) SCREW-IN PERICARDIAL LEADS AND SYSTEMS FOR DELIVERING SCREW-IN PERICARDIAL LEADS

(71) Applicant: Pacesetter, Inc., Sylmar, CA (US)

(72) Inventors: Gene A. Bornzin, Simi Valley, CA (US); Devan Hughes, Pasadena, CA (US); Keith Victorine, Valencia, CA (US); Zoltan Somogyi, Simi Valley, CA (US); Matthew Nojoomi, Los Angeles, CA (US); Ekaterina Tkatchouk, Beverly Hills, CA (US); Xiaoyi Min, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 666 days.

(21) Appl. No.: 17/069,102

(22) Filed: Oct. 13, 2020

(65) Prior Publication Data
US 2021/0031028 A1 Feb. 4, 2021

Related U.S. Application Data

(62) Division of application No. 15/937,431, filed on Mar. 27, 2018, now Pat. No. 10,835,741.

(51) Int. Cl.
| *A61N 1/05* | (2006.01) |
|---|---|
| *A61B 5/29* | (2021.01) |
| *A61N 1/39* | (2006.01) |
| *A61B 5/00* | (2006.01) |
| *A61N 1/37* | (2006.01) |

(52) U.S. Cl.
CPC ............ *A61N 1/059* (2013.01); *A61B 5/29* (2021.01); *A61N 1/3956* (2013.01); *A61B 5/686* (2013.01); *A61N 1/0573* (2013.01); *A61N 1/37* (2013.01)

(58) Field of Classification Search
None
See application file for complete search history.

(56) References Cited

U.S. PATENT DOCUMENTS

| 4,865,037 A | 9/1989 | Chin et al. |
|---|---|---|
| 4,922,927 A | 5/1990 | Fine et al. |
| 4,998,975 A | 3/1991 | Cohen et al. |
| 5,405,374 A | 4/1995 | Stein |
| 5,411,546 A | 5/1995 | Bowald et al. |
| 5,456,706 A | 10/1995 | Pless et al. |
| 5,609,621 A | 3/1997 | Bonner |
| 6,882,886 B1 | 4/2005 | Witte et al. |
| 2003/0139794 A1 | 7/2003 | Jenney et al. |

(Continued)

*Primary Examiner* — Kennedy Schaetzle
(74) *Attorney, Agent, or Firm* — Dean D. Small; The Small Patent Law Group, LLC

(57) ABSTRACT

Disclosed herein is a screw-in lead implantable in the pericardium of a patient heart and a system for delivering such leads to an implantation location. The leads include a helical tip electrode and a curvate body including a defibrillator coil with improved contact between the defibrillator coil and the patient heart. The delivery system includes a delivery catheter and lead receiving sheath disposed within the catheter. A fixation tine is disposed on one of the delivery catheter and the lead receiving sheath such that the delivery system may be anchored into the pericardium during fixation of the screw-in lead. In certain implementations, an implantable sleeve receives the leads to bias the defibrillator coil against the patient heart.

16 Claims, 15 Drawing Sheets

(56) References Cited

U.S. PATENT DOCUMENTS

| | | |
|---|---|---|
| 2004/0122497 A1 | 6/2004 | Zhang et al. |
| 2004/0260375 A1 | 12/2004 | Zhang et al. |
| 2006/0009827 A1* | 1/2006 | Kurth .................. A61N 1/0573 |
| | | 607/119 |
| 2006/0041299 A1 | 2/2006 | Bauer et al. |
| 2007/0239244 A1 | 10/2007 | Morgan et al. |
| 2010/0228330 A1 | 9/2010 | Bomzin |
| 2014/0187893 A1* | 7/2014 | Clark ................ A61M 25/0009 |
| | | 606/41 |
| 2015/0066125 A1 | 3/2015 | Osypka |
| 2016/0158567 A1 | 6/2016 | Marshall et al. |
| 2017/0239465 A1* | 8/2017 | Malone ................ A61N 1/056 |
| 2018/0256904 A1* | 9/2018 | Li ..................... A61M 25/0136 |

\* cited by examiner

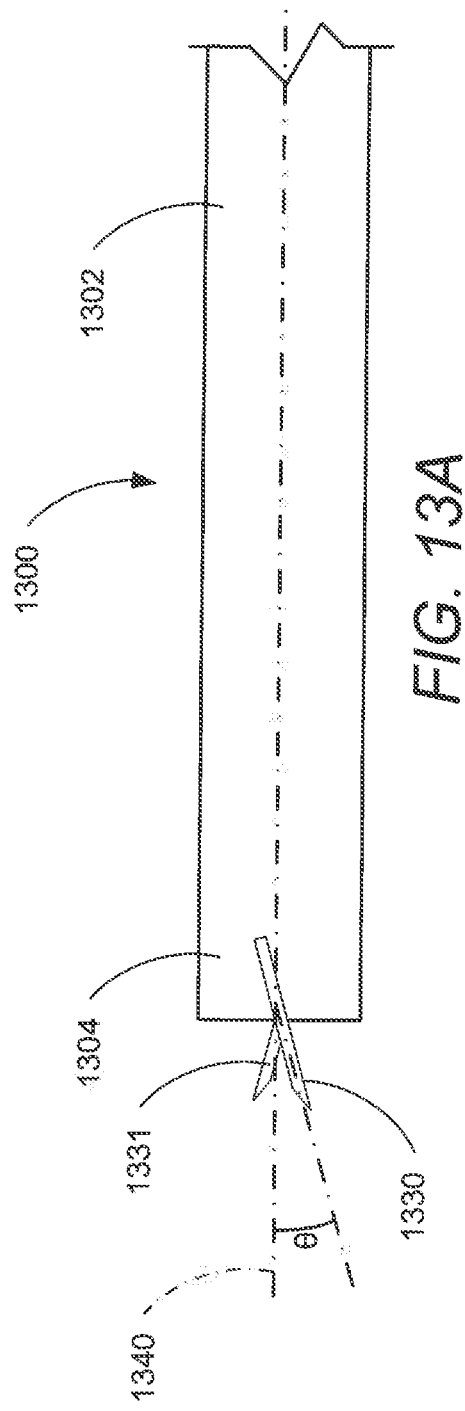
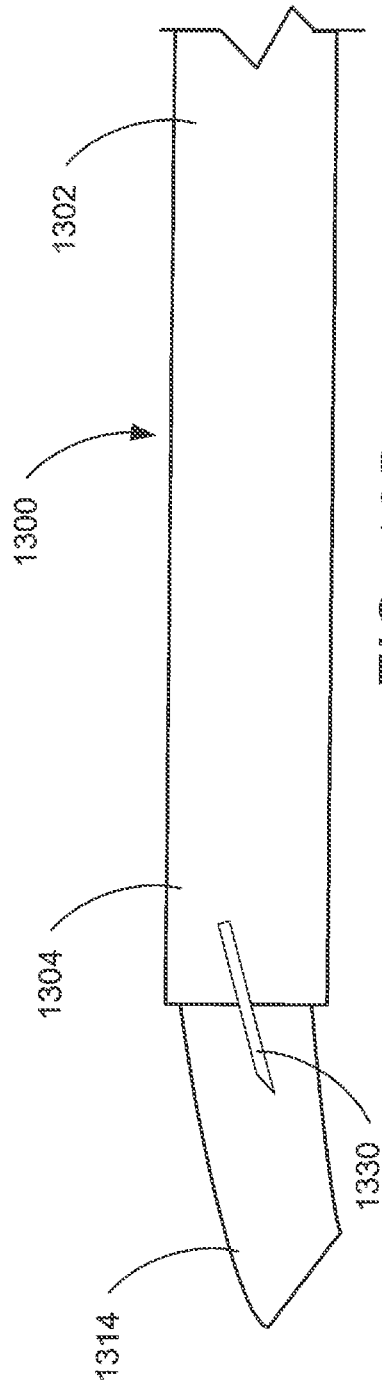

SCREW-IN PERICARDIAL LEADS AND SYSTEMS FOR DELIVERING SCREW-IN PERICARDIAL LEADS

REFERENCE TO RELATED APPLICATIONS

The present application is a divisional application of, and claims priority to, U.S. application Ser. No. 15/937,431, Titled "SCREW-IN PERICARDIAL LEADS AND SYSTEMS FOR DELIVERING SCREW-IN PERICARDIAL LEADS" which was filed on 27 Mar. 2018, the complete subject matter of which is expressly incorporated herein by reference in its entirety.

FIELD OF THE INVENTION

Aspects of the present invention relate to medical apparatus and methods. More specifically, the present invention relates to implantable medical leads for use in defibrillation and methods of delivering such leads.

BACKGROUND OF THE INVENTION

Cardiac defibrillation is a therapy aimed to control the refractory periods of cardiac myocytes, in order to extinguish electrical reentry currents that lead to a potentially lethal arrhythmia, known as ventricular fibrillation, within the heart. Defibrillation systems treat arrhythmia by delivering an electric current to the heart, which depolarizes musculature of the heart, interrupting the arrhythmia and enabling the sinoatrial node of the heart to re-establish a normal heart rhythm.

Several configurations of Implantable Cardioverter Defibrillator (ICD) systems have been developed to provide this therapy. ICD systems generally include a pulse generator and one or more implantable leads for delivering an electric current generated by the pulse generator. However, traditional ICD systems that include transvenous or subcutaneous leads present various issues regarding, among other things, infection, replacement of degraded leads, and effective delivery of electrical current during ventricular fibrillation.

Accordingly, there is a need in the art for implantable leads that improve electrical current delivery to the patient heart while reducing the likelihood of complications associated with known ICD systems. There is also a need in the art for associated delivery methods.

BRIEF SUMMARY OF THE INVENTION

Disclosed herein are electrotherapy systems including implantable medical leads adapted to be fixed to the pericardium of a patient heart and associated lead delivery systems.

In one embodiment, a delivery system for delivering an implantable medical lead to an implantation site on a pericardium of a patient heart is provided. The delivery system according to the present disclosure includes a delivery catheter, which may, in certain implementations be a steerable catheter. The delivery catheter includes a proximal end and a distal end opposite the proximal end and defines an inner lumen. The delivery system further includes a lead receiving sheath disposed within the lumen and shaped to receive the implantable medical lead. A fixation tine extends from one of the delivery catheter and the sheath for engaging the pericardium adjacent an implantation site of the implantable medical lead.

In one implementation of the delivery system, the lead receiving sheath defines a longitudinal axis and includes a sheath tip that directs an implantable medical lead inserted into the lead receiving sheath away from the longitudinal axis. The tip may include a reinforced curved surface that biases the lead away from the longitudinal axis and may include a tip wall including a score or similar feature adapted to facilitate splitting of the sheath in response to contact of the tip wall with the implantable medical lead and rotation of the implantable medical lead within the sheath.

In another implementation, the fixation tine may be one of a plurality of fixation tines distributed about the delivery catheter of the sheath. The fixation tine may extend a predetermined amount beyond the delivery catheter of the sheath and at a predetermined angle relative to a longitudinal axis of the delivery catheter or the sheath. In certain implementations, the delivery system may include an obturator disposed at the distal end of the delivery catheter or the sheath and that extends beyond the fixation tine to prevent the fixation tine catching on adjacent tissue during insertion of the delivery system into the mediastinum.

In another embodiment, an implantable medical lead fixable to a pericardium of a patient heart is provided. The implantable medical lead includes a helical tip electrode, a distal lead portion extending from the helical tip electrode, a curvate section extending from the distal lead portion and a proximal lead portion proximal the curvate section. The curvate section includes a defibrillator coil and is formed into a generally s-shaped curve including both curved and substantially straight segments. In certain implementations, the segments of the curvate section have lengths (for the straight segments) and radii of curvature and arc lengths (for the curved segments) within predetermined ranges for providing defibrillation through the pericardium. The dimensions of the helical tip electrode may also adhere to predetermined ranges for facilitating fixation of the implantable medical lead into the pericardium.

In one implementation, the implantable medical lead may further include a distal ring electrode proximal the helical tip electrode and a pair of proximal ring electrodes proximal the defibrillator coil. In another implementation, each of the distal lead portion and the proximal lead portion may comprise a braided cable interwoven with polyethylene terephthalate and the defibrillator coil comprises platinum windings with a co-polymer of polyurethane and silicone disposed between adjacent windings.

In yet another embodiment, an implantable medical lead assembly for fixation of one or more medical leads to a pericardium of a patient heart and for use in providing electrotherapy to the patient heart is provided. The implantable medical lead assembly includes a lead body having a distal segment including a defibrillator coil and a proximal segment opposite the distal segment. The assembly further includes a sleeve defining a lumen through which the lead body extends. The sleeve is adapted to be fixed in proximity to the patient heart and includes each of a first sleeve segment and a second sleeve segment distal the first sleeve segment. The second sleeve segment extends at an angle relative a longitudinal axis of the first sleeve segment and is shaped to bias the defibrillator coil against the pericardium when fixed in proximity to the patient heart. In one implementation, the assembly includes a second lead body and the sleeve further defines a second lumen substantially parallel to the lumen through which the second lead body extends.

BRIEF DESCRIPTION OF THE DRAWINGS

FIGS. 13A-13D are plan views of a distal portion of a third delivery system in accordance with the present disclosure.

DETAILED DESCRIPTION

Figure 1:
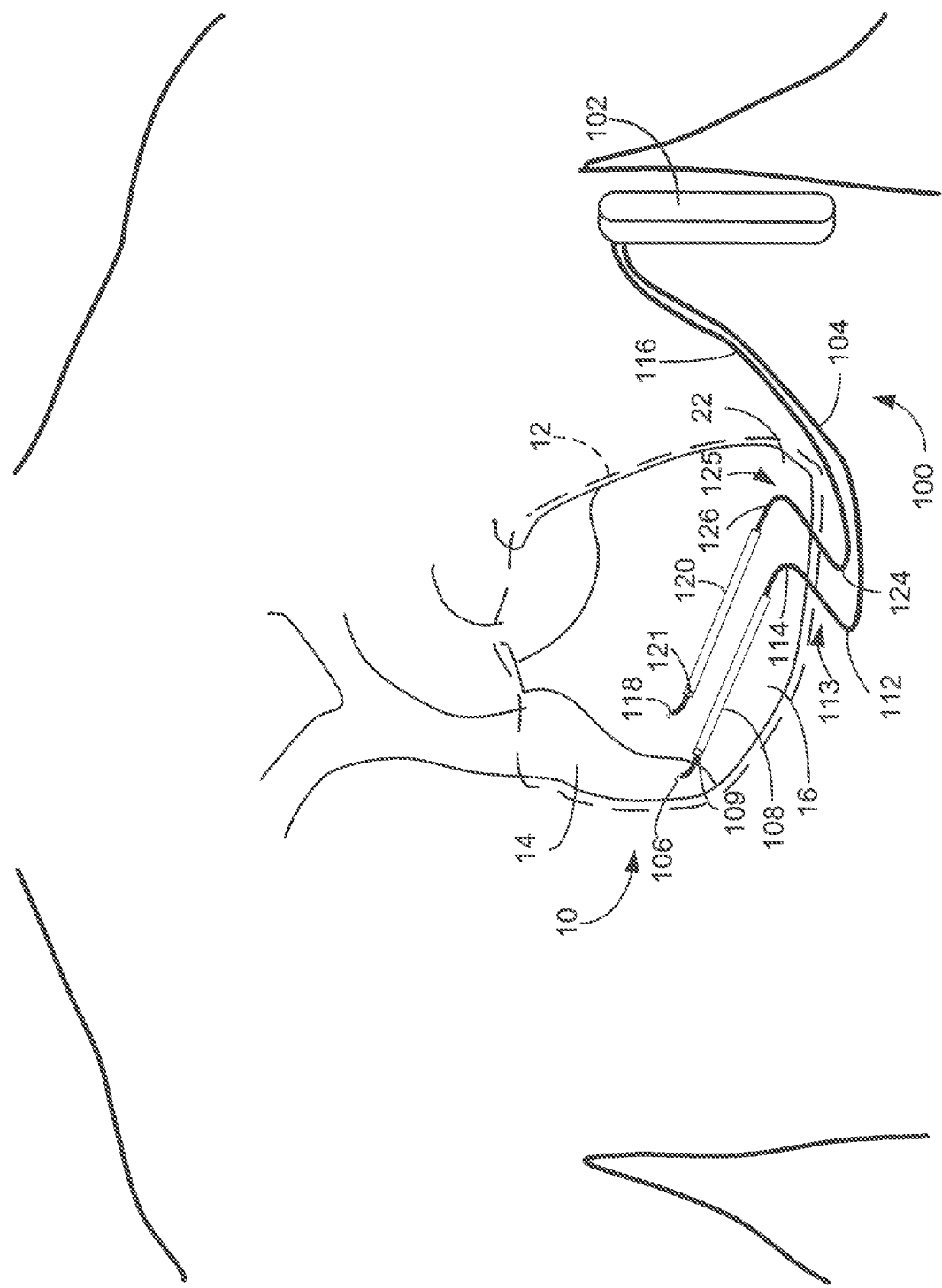
FIG. 1 is a diagrammatic depiction of a first embodiment of an electrotherapy system electrically coupled to a patient heart as shown in an anterior view.

Several configurations of Implantable Cardioverter Defibrillator (ICD) systems have been developed to provide electrotherapy to a patient heart. However, such known configurations present various issues to the patient and healthcare providers tasked with implanting and maintaining the ICD systems.

Transvenous defibrillation systems consist of electrodes and corresponding leads that are introduced into the heart through vasculature, such as the superior vena cava, and fixated within different chambers of the heart. For patients who have complex cardiac venous anatomy, tricuspid valve defects, kidney disease, superior venous stenosis (such as vena cava syndrome), or similar conditions, transvenous ICD systems are contraindicated. Even if such contraindications are not present, transvenous ICD systems are prone to complications attributable to infection and lead longevity. When lead replacement or removal is required due to infection or lead malfunction, for example, transvenous leads are dangerous to remove and present the potential for severe cardiovascular venous and valvular damage during the removal procedure. Moreover, the implantation of transvenous defibrillation systems in juveniles at risk of ventricular fibrillation proves challenging as the cardiac vasculature of such patients may be too small or underdeveloped. Moreover, cardiac and thorax growth of such patients can provide additional complications should a transvenous system be implanted. For example, over time and as the juvenile patient grows, it is not uncommon for the energy required to defibrillate the patient to exceed the capability of the originally implanted ICD system.

Subcutaneous ICD systems have also been developed, yet still present various issues and complications. The electrodes of subcutaneous ICD systems are implanted in the thorax just below the skin. While reducing the likelihood of infection and damage associated with transvenous ICD systems, the placement of the electrode in a subcutaneous ICD system requires higher energy to deliver sufficient current to the heart for successful defibrillation. For example, commercial subcutaneous pulse generators may be required to provide up to 1350 V as compared to transvenous ICD systems, which may require up to 900 V. The increased power requirements also contribute to the increased size and electrical complexity of subcutaneous ICD systems. Due to the implant location, subcutaneous ICD systems are also generally unable to provide anti-tachycardia pacing, which can provide therapy to truncate monomorphic ventricular tachycardia before it progresses into lethal ventricular fibrillation. Moreover, for the clinician and the patient, the subcutaneous system has more incisions than the transvenous system, which presents more potential locations for infection sites, and more wounds requiring post-operative care and healing.

The implantable medical leads described herein address the complications of the ICD systems mentioned above. For example, the implantable medical leads provide a solution for juvenile patients or adult patients with complex cardiac venous or valvular anatomy as the leads do not require access to the vasculature leading to the heart. Certain implementations of the leads are further designed to be removable, such as by including smooth, flat coil electrodes, and to reduce likelihood of infection and encapsulation by including a coating to minimize the foreign body response.

The implantable medical leads described herein are implanted into the exterior surface of the pericardium and, as a result, reduce both the likelihood and potential severity of infections as compared to transvenous leads. The leads are designed to fasten into the pericardium using a helical screw electrode disposed on the end of the lead that is advanced into the tissue by rotating the entire lead. Fixation of the helical screw electrode may be facilitated by use of one or more of a steerable catheter, a sheath that redirects the helical screw electrode, and fixation tines disposed on either the delivery catheter or the sheath.

When anchored, a defibrillator coil of the lead is made to abut the pericardium, thereby providing improved transfer of current from the defibrillator coil into the muscular tissues of the heart. In certain implementations, contact between the defibrillator coil and the pericardium is achieved, in part, by the implantable lead being sandwiched between the pericardium and tissue of the mediastinum. Contact between the defibrillator coil and the pericardium may also be facilitated by the lead being formed of a semi-rigid material that may be bent into a shape that conforms to the heart or otherwise biases the lead against the heart. Additional support structures, such as suture sleeves, may also be installed within the mediastinum adjacent the heart to support and route the implantable lead to improve contact between the defibrillator coil and the pericardium.

Implantable medical leads according to this disclosure have exhibited defibrillation threshold (DFT) values (which correspond to the energy output of the ICD required to defibrillate the heart back to sinus rhythm) that are equivalent to or, in certain cases, lower than those of conventional transvenous ICD systems. Such lower DFT values allow for the use of lower powered and smaller form factor pulse generators which improve the comfort and overall safety of the patient.

Improved DFT values are also realized when the disclosed leads and ICD systems are compared to conventional subcutaneous ICD systems. As previously noted, leads of conventional subcutaneous ICD systems are implanted under the skin of the thorax. In contrast, ICD systems in accordance with this disclosure provide more direct contact between defibrillation coils and the heart. As a result, the distance and structures through which current must pass to reach the heart are reduced in comparison to conventional ICD systems, thereby reducing the DFT. Moreover, unlike conventional ICD systems, the proximity with which the leads are implanted relative to the heart enables sensing and pacing functionality.

A non-limiting discussion regarding various arrangements of electrotherapy systems in accordance with this disclosure are provided with reference to FIGS. 1-7. A subsequent non-limiting discussion with reference to FIGS. 8A-13D will address further details of leads and delivery devices in accordance with this disclosure and which may be used to achieve the arrangements illustrated in FIGS. 1-7. Unless otherwise noted, the example configurations illustrated in FIGS. 1-7 may be used to provide one or more of sensing, pacing, and defibrillation functionality and may be modified to provide any combination thereof.

Reference is first made to FIG. 1, which is a diagrammatic depiction of an electrotherapy system 100 electrically coupled to a patient heart 10 as shown in an anterior view. As shown in FIG. 1, the system 100 includes an implantable pulse generator (e.g., pacemaker, implantable cardioverter defibrillator ("ICD"), or etc.) 102 and one or more (e.g., two) implantable medical leads 104, 116 electrically coupling the patient heart 10 to the pulse generator 102. In addition to providing defibrillation, the system 100 of FIG. 1 may operate as a "DDD"-type pacemaker in which pacing and sensing are provided for both a right atrium ("RA") 14 and a right ventricle ("RV") of the heart 10 in a dual response mode.

The system 100 includes an RA lead 104 that is screwed into the pericardium 12 of the heart 10 near the RA 14 using an RA helical tip electrode 106 disposed on a distal end of the RA lead 104. In certain implementations, the RA helical tip electrode 106 may be screwed through the pericardium 12 into the underlying epicardium and, in certain implementations, further into the myocardium. The RA lead 104 includes a first defibrillator coil 108 proximal the helical tip electrode 106 and a ring electrode 109 disposed between the helical tip electrode 106 and the first defibrillator coil 108. The system 100 further includes an RV lead 116 that is similarly screwed into the pericardium 12 of the heart 10 (or through the pericardium 12 into the underlying epicardium and myocardium) near the RV 16 using an RV helical tip electrode 118. The RV lead 116 further includes a second defibrillator coil 120 proximal the RV helical tip electrode 118 and an RV ring electrode 121 disposed between the RV helical tip electrode 118 and the second defibrillator coil 120. The electrotherapy system 100 further includes a pulse generator 102 implanted in a subaxillary location. Each of the RA lead 104 and the RV lead 116 are coupled to the pulse generator 102 such that the RA lead 104 and the RV lead extend medially from the pulse generator 102 towards the heart 10.

During operation, defibrillation may be achieved by providing current along various vectors. For example, in certain implementations, current may be passed between the first defibrillator coil 108 and the second defibrillator coil 120, between the first defibrillator coil 108 and the pulse generator 102, and/or between the second defibrillator coil 120 and the pulse generator 102.

As previously noted, the electrotherapy system 100 further provides for sensing and pacing of the RA 14 and the RV 16. More specifically, sensing and pacing of the RA may be conducted by detecting and providing electrical stimulation, respectively, between the RA tip electrode 106 and the RA ring electrode 109. Similarly, sensing and pacing of the RV 16 may be conducted by detecting and providing electrical stimulation, respectively, between the RV tip electrode 118 and the RV ring electrode 121.

Each of the RA lead 104 and the RV lead 116 may include a pre-shaped bend proximal their respective defibrillator coils 108, 120. As shown in FIG. 1, for example, the RA lead 104 includes an RA lead proximal bend 112 and an RA distal bend 114 that together form a "z"-shaped section 113 of the RA lead 104. Similarly, the RV lead 116 includes an RV proximal bend 124 and an RV distal bend 126 that together form a "z"-shaped section 125 of the RV lead 116. In certain implementations, the z-shaped sections 113 and 125 may have a gauge from and including 8 Fr to and including 12 Fr to increase stability of the RA lead 104 and the RV lead 116 against the heart 10. In certain implementations, the RV distal bend 126 and the RA distal bend 114 may be from and including 45 degrees to and including 135 degrees and may each have a radius from and including 7 millimeters (mm) to and including 20 mm. The RV lead proximal bend 124 and the RA lead proximal bend 112 may be from and including 45 degrees to and including 135 degrees and may each have a radius from and including 7 mm to and including 2 mm. The length of the segments between the bends of each lead 104, 116 may be from and including 5 mm to and including 70 mm, with each bend being in substantially opposite directions.

Figure 2:
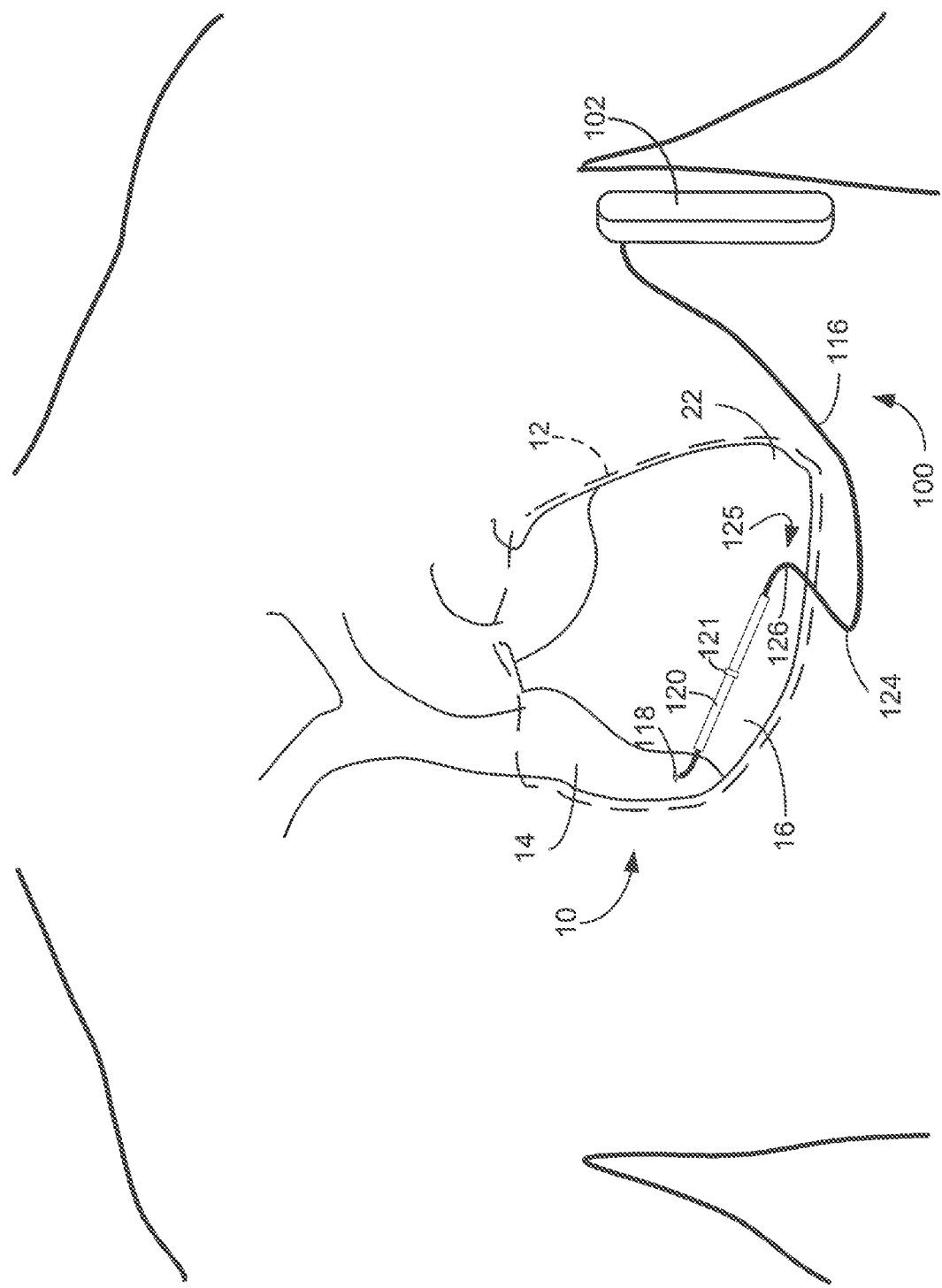
FIG. 2 is a diagrammatic depiction of a second embodiment of an electrotherapy system electrically coupled to a patient heart as shown in an anterior view.

Reference is next made to FIG. 2, which is a diagrammatic depiction of the electrotherapy system 100 according to a second implementation of the present disclosure. Similar to FIG. 1, the electrotherapy system 100 of FIG. 2 is configured to provide defibrillation, however, in contrast to the DDD configuration shown in FIG. 1, the system 100 is illustrated in FIG. 2 as having a "VVI" pacing configuration in which sensing and pacing are provided only to the RV 16 and the implantable pulse generator 102 operates in an inhibited triggering mode.

The electrotherapy system 100 of FIG. 2 includes an RV lead 116 including an RV helical tip electrode 118, a defibrillator coil 120 proximal the RV helical tip electrode 118, and a ring electrode 121 disposed along the defibrillator coil 120. The RV lead 116 is further coupled to a subaxillary pulse generator 102. During operation, defibrillation is provided by passing current between the defibrillator coil 120 and the pulse generator 120. Sensing and pacing of the RV 16 may be conducted by detecting and providing electrical stimulation, respectively, between the RV tip electrode 118 and the RV ring electrode 121. In certain implementations, the RV lead 116 may further include an RV proximal bend 124 and an RV distal bend 126 that together form a "z"-shaped section 125 of the RV lead 116 to provide additional support to the RV lead 116 and to bias the defibrillator coil 120 against the pericardium 12.

Figure 3:
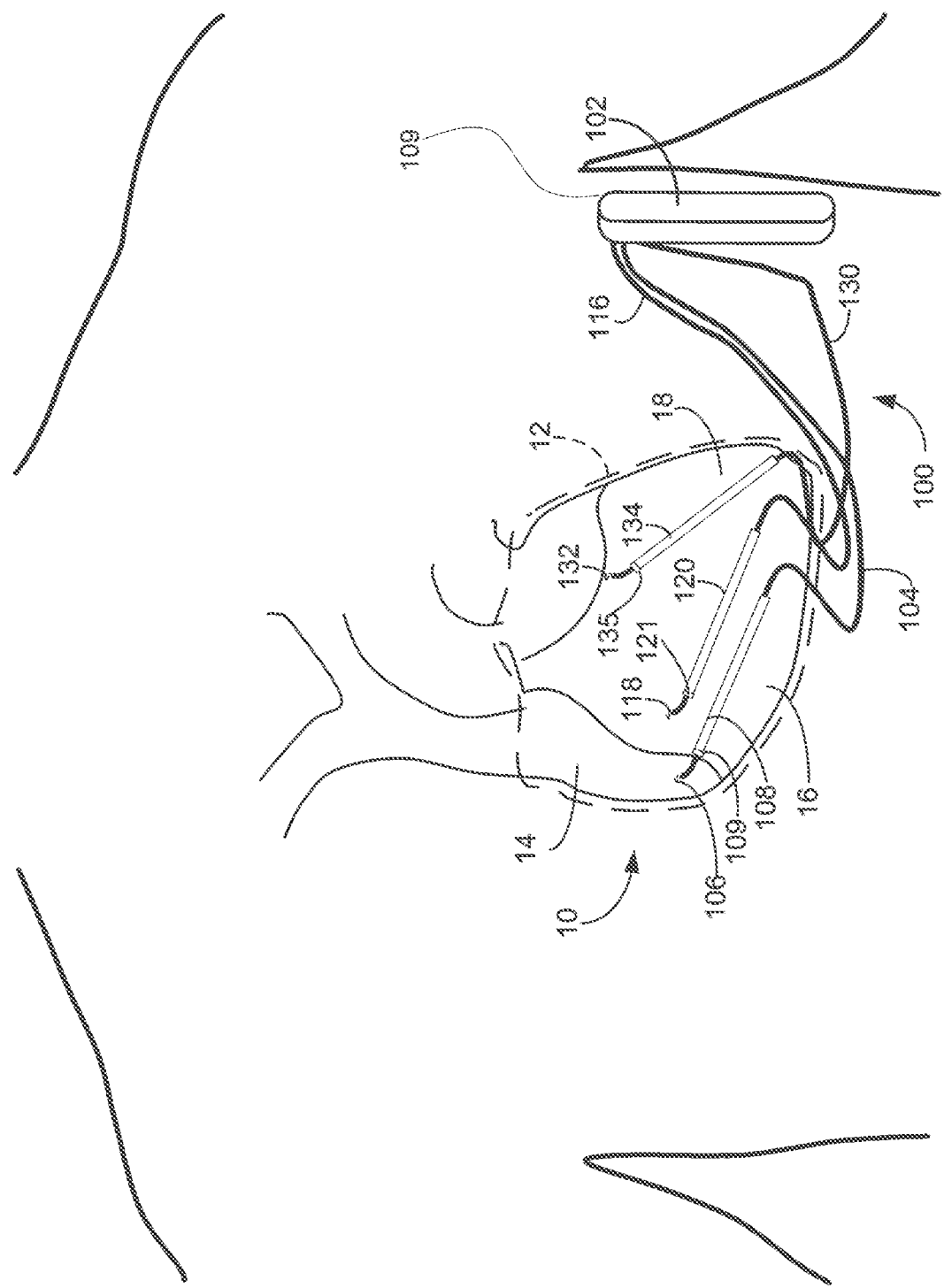
FIG. 3 is a diagrammatic depiction of a third embodiment of an electrotherapy system electrically coupled to a patient heart as shown in an anterior view.

Reference is next made to FIG. 3, which is a diagrammatic depiction of the electrotherapy system 100 according to a third implementation of the present disclosure. As illustrated in FIG. 3, the electrotherapy system 100 is adapted to provide cardiac resynchronization therapy (CRT).

The system 100 of FIG. 3 includes an RA lead 104 including an RA helical tip electrode 106 disposed on a distal end of the RA lead 104, the RA helical tip electrode 106 being screwed into the pericardium 12 of the RA 14 or through the pericardium 12 into the underlying epicardium and myocardium. The RA lead 104 further includes a first defibrillator coil 108 proximal the RA helical tip electrode 106 and a ring electrode 109 disposed between the helical tip electrode 106 and the first defibrillator coil 108. Accordingly, during operation, pacing and sensing of the RA 14 may be provided by monitoring and providing electrical stimulation between the RA helical tip electrode 106 and the ring electrode 109.

The system 100 of FIG. 3 further includes an RV lead 116 that is similarly screwed into the pericardium 12 of the heart 10 (or through the pericardium 12 into the underlying epicardium and myocardium) near the RV 16 using an RV helical tip electrode 118. The RV lead 116 also includes a second defibrillator coil 120 and an RV ring electrode 121 that provides sensing and pacing functionality in conjunction with the RV helical tip electrode 118.

To facilitate synchronization of the RV 16 and a left ventricle (LV) 18 of the heart 10, the system 100 also includes an LV lead 130 including an LV helical tip electrode 132 disposed on a distal end of the LV lead 130, the LV helical tip electrode 132 being screwed into the pericardium 12 of the LV 18 or through the pericardium 12 into the underlying epicardium and myocardium. The LV lead 130 also includes a third defibrillator coil 134 and an LV ring electrode 135 that provides sensing and pacing functionality in conjunction with the LV helical tip electrode 132.

As illustrated in FIG. 3, each of the RA lead 104, the RV lead 116, and the LV lead 130 are coupled to a subaxillary pulse generator 102 and extend medially therefrom towards the heart 10. During operation, defibrillation may be provided between any two of the first defibrillator coil 108, the second defibrillator coil 120, the third defibrillator coil 134, and the pulse generator 102.

Figure 4:
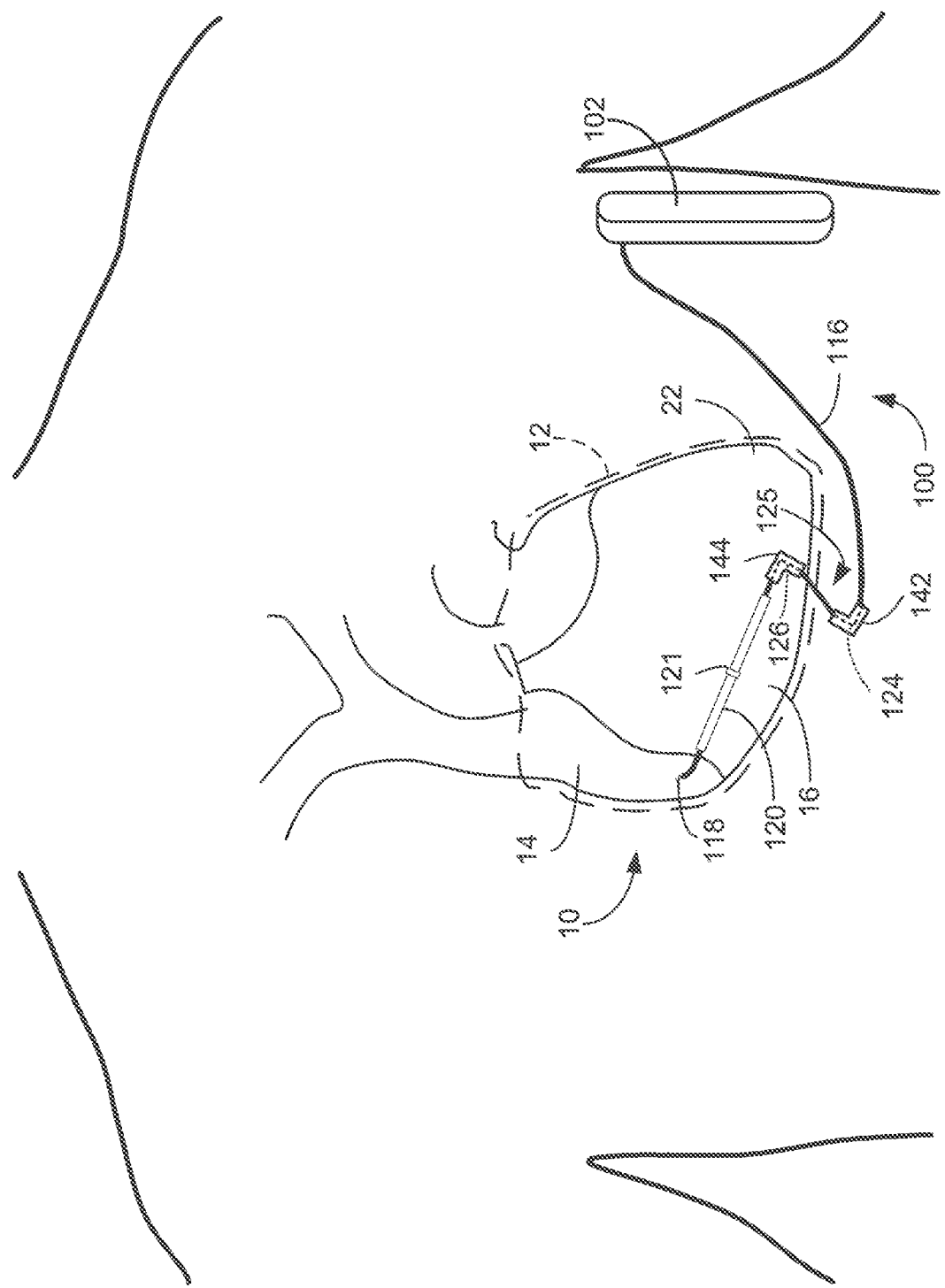
FIG. 4 is a diagrammatic depiction of a fourth embodiment of an electrotherapy system electrically coupled to a patient heart as shown in an anterior view.

Reference is next made to FIG. 4, which is a diagrammatic depiction of the electrotherapy system 100 according to a fourth implementation of the present disclosure. The implementation of the system 100 in FIG. 4 is directed to providing defibrillation in a WI-type configuration in which pacing and sensing is conducted on the RV 16 in an inhibited triggering mode. Similar to the implementation illustrated in FIG. 2, the RV lead 116 of FIG. 4 includes an RV ring electrode 121 disposed along an RV defibrillator coil 120. Accordingly, sensing and pacing may be provided between the RV helical tip electrode 118 and the RV ring electrode 121 and defibrillation may be provided between the defibrillator coil 120 and a subaxillary pulse generator 102 to which the RV lead 116 is coupled.

The RV lead 116 includes an RV proximal bend 124 and an RV distal bend 126 that together form a "z"-shaped section 125 of the RV lead 116. In the implementation of FIG. 4, the z-shaped section 125 is achieved, in part, through the use of a proximal RV suture sleeve 142 and a distal RV suture sleeve 144. For example, each of the proximal RV suture sleeve 142 and the distal RV suture sleeve 144 may be clamshell or similar suture sleeves that may be closed around a portion of the RV lead 116 proximal the defibrillator coil 120. After insertion of the RV lead 116, each of the proximal RV suture sleeve 142 and the distal RV suture sleeve 144 may be sutured to tissue adjacent the heart, such as the inner wall of the mediastinum. In contrast to the implementation of FIG. 1 in which the leads 104, 116 were pre-shaped to form their respective bends, when using the suture sleeves 142, 144 the lead bends 124, 125 may be imparted by suture sleeves 142, 144.

The suture sleeves 142, 144 may be substantially cylindrical in shape and may be pre-loaded over the lead body prior to assembly of the lead 116. This allows for sliding of the suture sleeves 142, 144 over the lead body to adjust the location of each bend 124, 126 and the lead segment extending between the bends 124, 126. The suture sleeves 142, 144 may be from and including 20 mm to and including 70 mm in length and may have a bend from and including 45 degrees to and including 135 degrees. Variations of the suture sleeves 142, 144 may include a single slit that allows for manually sliding of the lead 116 inside of the cylindrical body of the suture sleeve after lead assembly and then tying of a suture around the circumference of the suture sleeve to maintain the suture sleeve on the lead and to prevent the lead body from exiting the suture sleeve. The implanter may choose to suture one or both suture sleeves 142, 144. In certain implementations, the suture sleeves 142, 144 may be made of one or more of polyurethane, silicone rubber, or a silicone polyurethane copolymer, such as Optim™.

Figure 5:
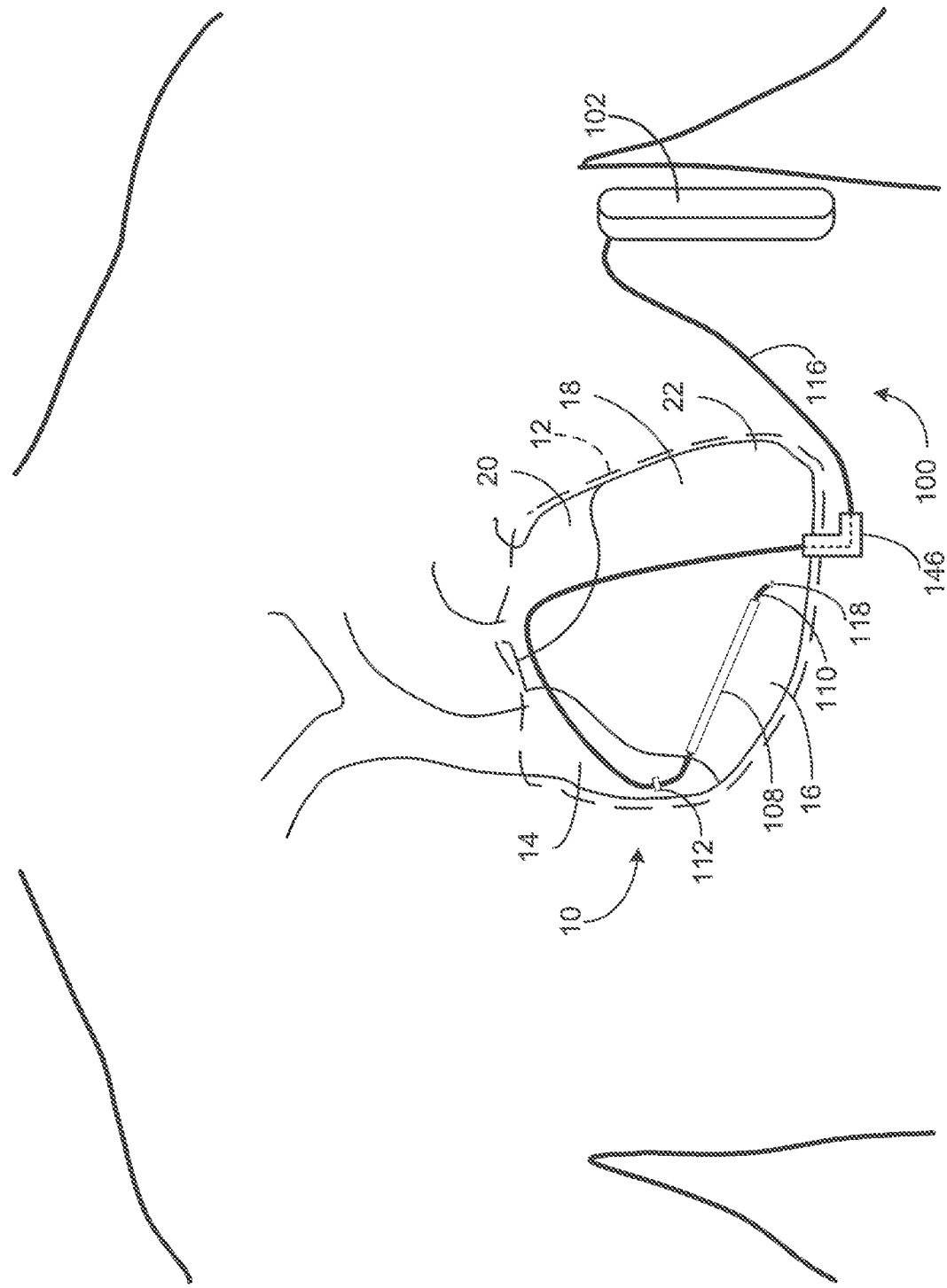
FIG. 5 is a diagrammatic depiction of a fifth embodiment of an electrotherapy system electrically coupled to a patient heart as shown in an anterior view.

Reference is next made to FIG. 5, which is a diagrammatic depiction of the electrotherapy system 100 according to a fifth implementation of the present disclosure. The implementation of the system 100 in FIG. 5 is directed to providing defibrillation and electrotherapy in a WI configuration in which pacing and sensing is conducted on the RV 16 in an inhibited triggering mode.

The implementation of FIG. 5 illustrates an alternative implantation to the WI configuration illustrated in FIG. 4. In FIG. 4, the z-shaped section 125 of the RV lead 116 formed by the RV suture sleeves 142, 144 routed the RV lead 116 substantially along the RV 16 such that the RV helical tip electrode 118 is affixed adjacent the RA 14. In contrast, the implementation of the electrotherapy system 100 shown in FIG. 5 includes a more circuitous routing of the RV lead 116. More specifically, an RV suture sleeve 146 fixed to tissue adjacent the apex 22 of the heart 10 stabilizes the RV lead 116 and routes the RV lead 116 substantially along the LV 18 towards a left atrium ("LA") 20 of the heart 10. The RV lead 116 then extends medially across the heart 10 towards the RA 18 before turning again to extend across the RV 16. The RV lead 116 is then affixed by screwing the RV helical tip electrode 118 into the pericardium 12 (or through the pericardium 12 into the underlying epicardium and myocardium) near the RV 16.

Reference is next made to FIG. 6, which is a diagrammatic depiction of the electrotherapy system 100 according to a sixth implementation of the present disclosure. The implementation of the system 100 in FIG. 6 is directed to providing electrotherapy including defibrillation and pacing and sensing in a DDD configuration in which pacing and sensing is conducted on both the RA 14 and the RV 16 in a dual response mode.

The system 100 includes an RA lead 104 that is screwed into the pericardium 12 of the heart 10 (or through the pericardium 12 into the underlying epicardium and myocardium) near the RA 14 using an RA helical tip electrode 106 disposed on a distal end of the RA lead 104. The RA lead 104 includes a defibrillator coil 108 proximal the helical tip electrode 106 and a ring electrode 109 disposed between the helical tip electrode 106 and the defibrillator coil 108. The system 100 further includes an RV lead 116 that is similarly screwed into the pericardium 12 of the heart 10 (or through the pericardium 12 into the underlying epicardium and myocardium) near the RV 16 using an RV helical tip electrode 118. The RV lead 116 further includes an RV ring electrode 121 disposed proximal the RV helical tip electrode 118. The electrotherapy system 100 further includes a pulse generator 102 implanted in a subaxillary location. Each of the RA lead 104 and the RV lead 116 are coupled to the pulse generator 102 such that the RA lead 104 and the RV lead extend medially from the pulse generator 102 towards the heart 10.

Figure 6A:
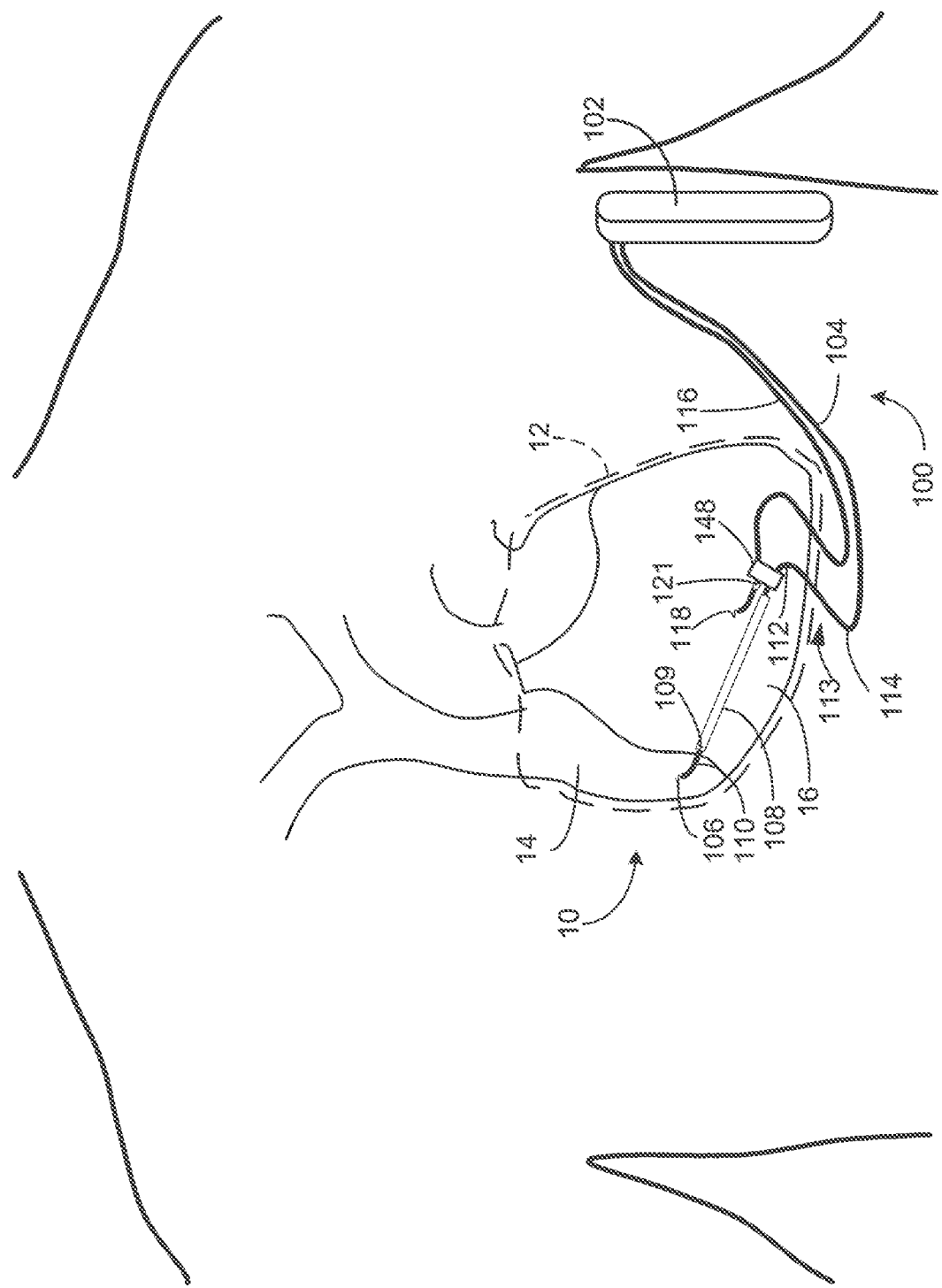
FIG. 6A is a diagrammatic depiction of a sixth embodiment of an electrotherapy system electrically coupled to a patient heart as shown in an anterior view.

The system 100 of FIG. 6A includes an RA lead 104 that is screwed through or into the pericardium 12 of the heart 10 into the RA 14 for pacing and sensing of the RA 14. The system 100 further includes an RV lead 116 screwed into the base of the RV 16 for pacing and sensing of the RV 16. The electrotherapy system 100 further includes a pulse generator 102 implanted in a subaxillary location. The RA lead 104 and the RV lead 116 are coupled to the pulse generator 102 and extend medially from the pulse generator towards the heart 10.

A cinch sleeve 148 is disposed about each of the RA lead 104 and the RV lead 116 proximal each of the RA defibrillator coil 108 and the RV ring electrode 121, forming a junction point between the RA lead 104 and the RV lead 116. The cinch sleeve 148 couples the RA lead 104 to the RV lead 116 such that the RA lead 104 and the RV lead 116 are maintained in a consistent position relative to each other. The cinch sleeve 148 may further be sutured or coupled to tissue adjacent the heart 10 to anchor the cinch sleeve 148 relative to the heart 10. By constraining the RA lead 104 near the apex 22 of the heart 10, the cinch sleeve 148 may also be used to urge the RA defibrillator coil 108 against the heart 10, thereby maintaining contact between the RA defibrillator coil 108 and the pericardium 12.

Figure 6B:
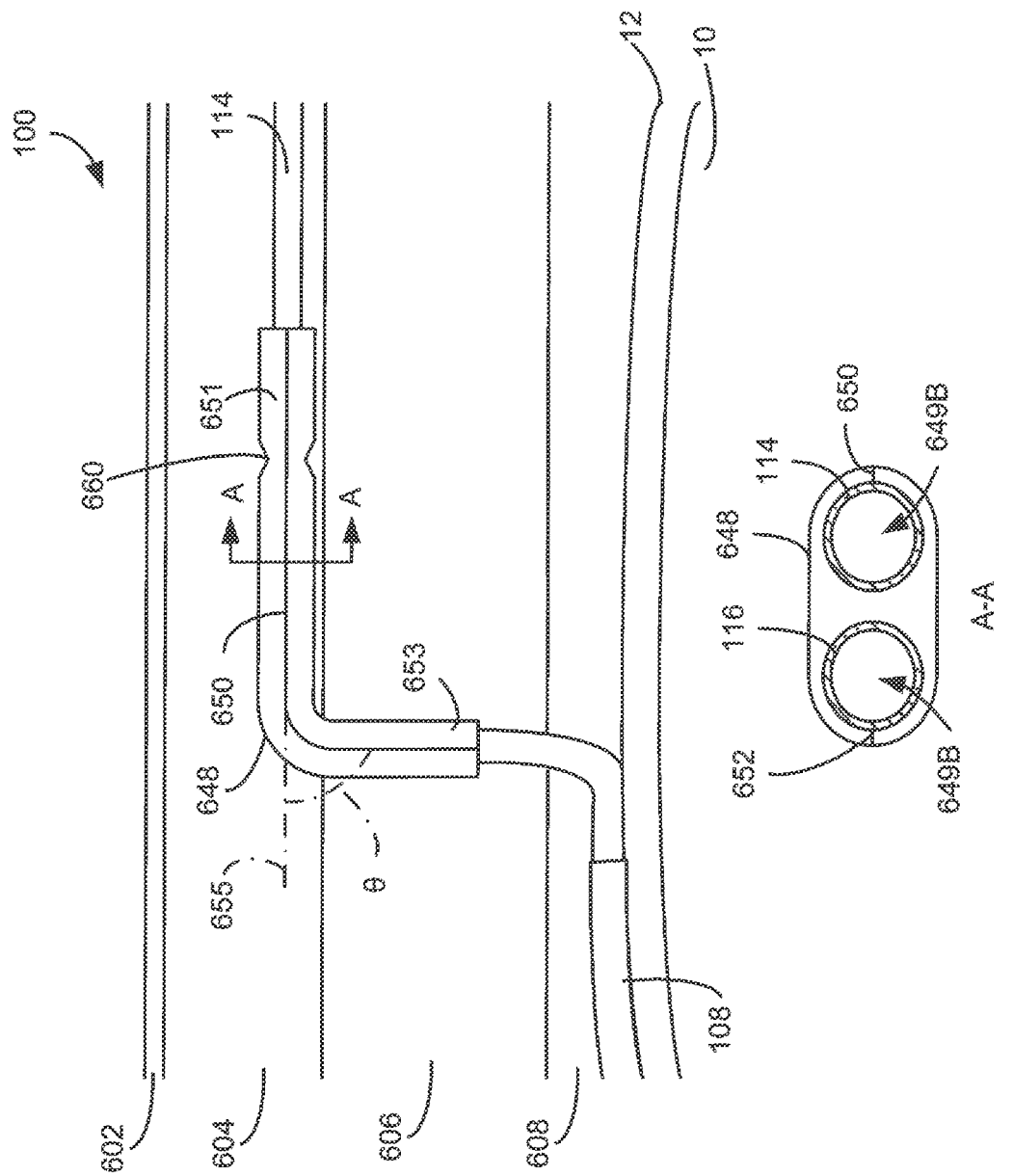
FIG. 6B is a transverse cross-sectional view of the patient heart of FIG. 6A and adjacent tissues including a sleeve adapted to receive the leads of the electrotherapy system of FIG. 6A.

FIG. 6B illustrates an implementation of the system 100 of FIG. 6A including an alternative sleeve 648. More specifically, FIG. 6B is a cross-sectional view of an implant site of the system along a transverse plane. The view includes each of the skin 602, subcutaneous fat 604, muscle 606, and mediastinum 608 in the anterior the heart 10. As illustrated by cross-section A-A, the sleeve 648 may define two cylindrical lumens 649A, 649B that extend substantially parallel to each other and that are shaped to receive respective leads 114, 116. In certain implementations, the sleeve 648 may include longitudinal slits 650, 652 to facilitate insertion of the leads 114, 116 into the sleeve 648. The sleeve 648 may also be pre-formed into an L- or similar bent shape including a first segment 651 and a second segment 653 in which the second segment 653 is disposed at an angle θ from and including 50 degrees to and including 90 degrees relative to a longitudinal axis 655 defined by the first segment 651. Accordingly the distal section of the sleeve 648 is directed substantially toward the heart 10 while the proximal section of the sleeve 648 extends substantially parallel to the body surface 610. As a result of the bent shape of the sleeve 648, urges the shocking coil 108 of the lead against the pericardium 12 of the heart 10. As shown in FIG. 6B, the sleeve 648 may further include a notch 660 about which a suture may be looped to fix the location of the sleeve 648 within the patient.

Figure 7:
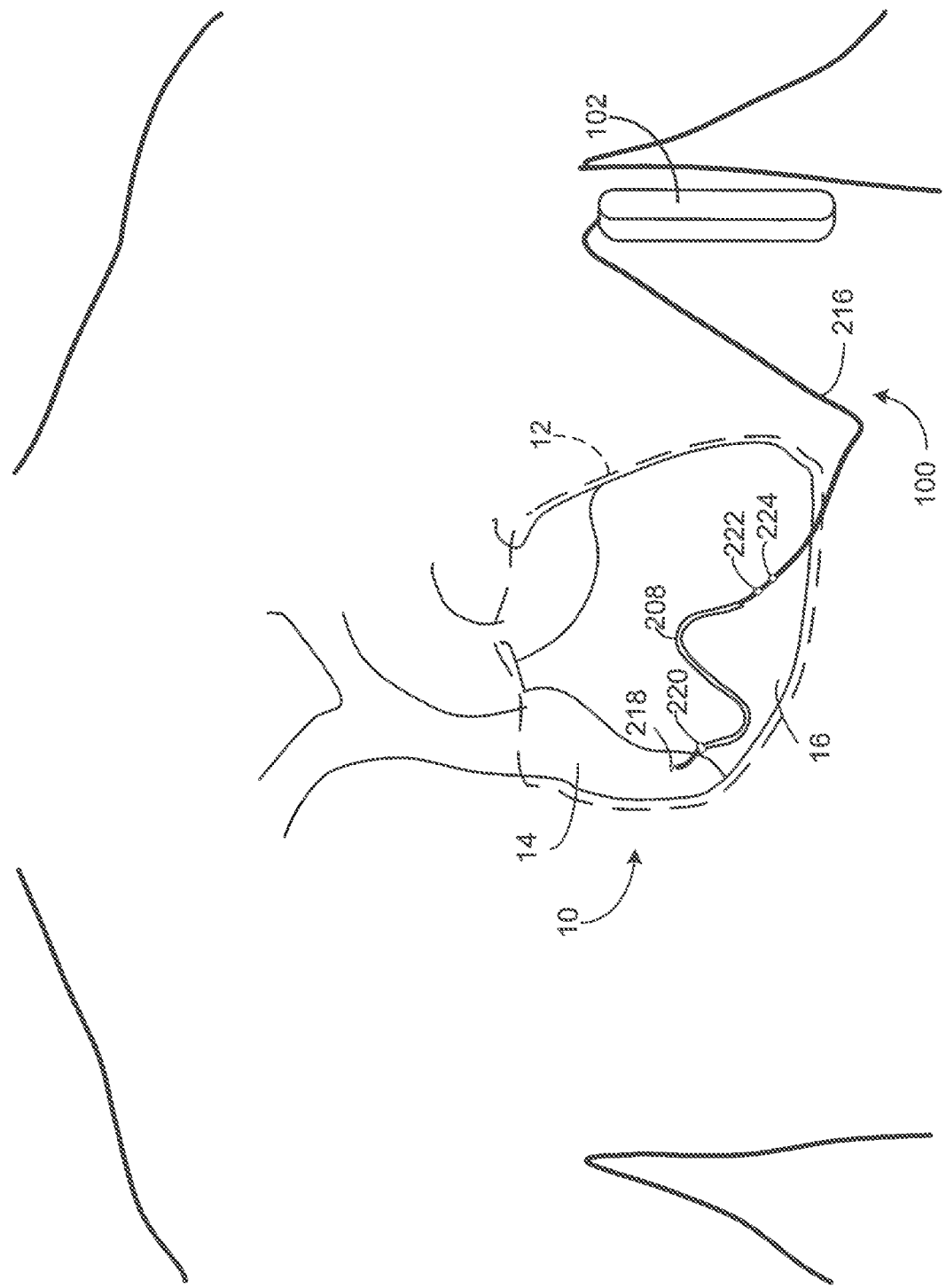
FIG. 7 is a diagrammatic depiction of a seventh embodiment of an electrotherapy system electrically coupled to a patient heart as shown in an anterior view.
Figure 8:
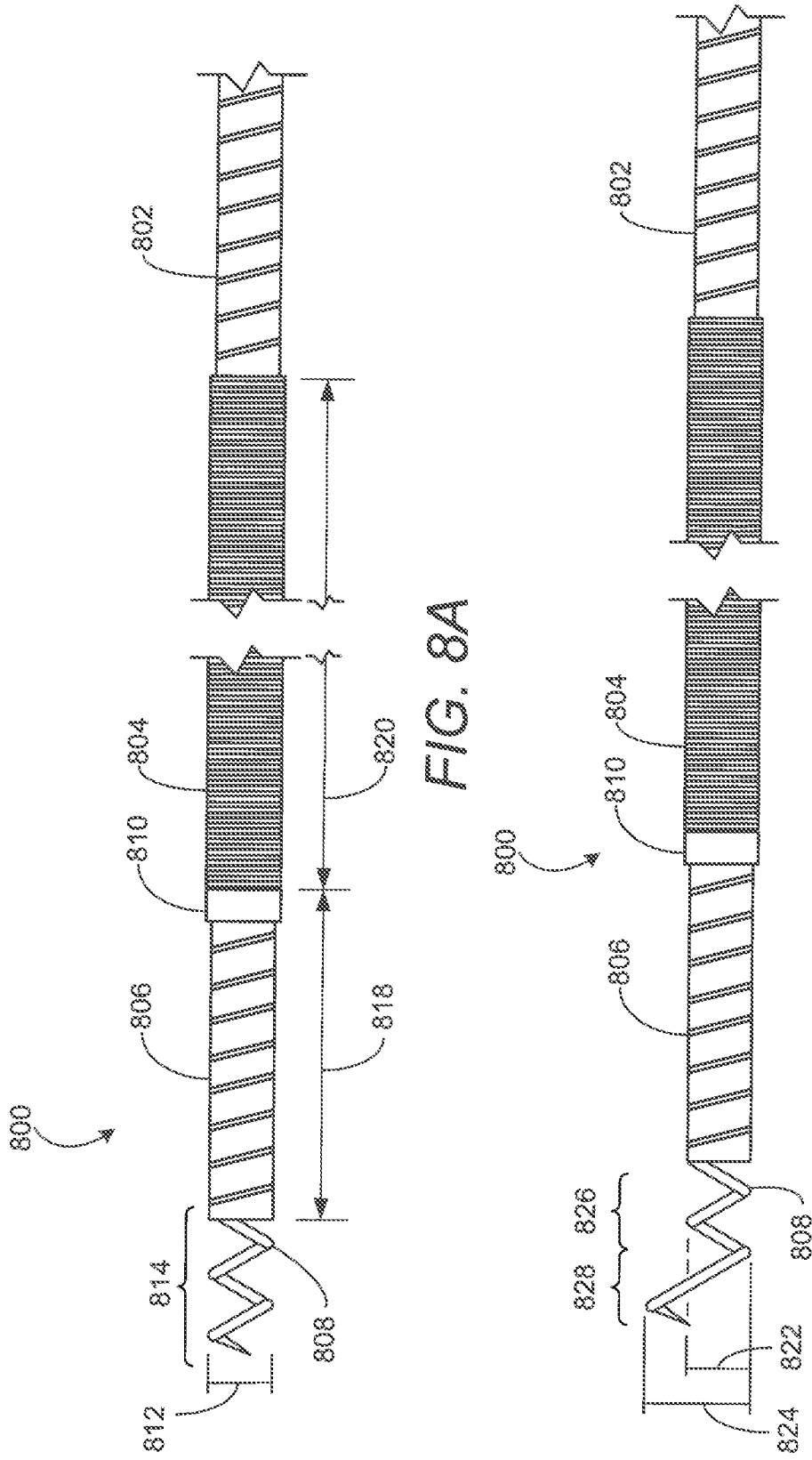
FIGS. 8A-8B are plan views of implantable medical leads for use in the electrotherapy systems of FIGS. 1-7.

Reference is next made to FIG. 7, which is a diagrammatic depiction of the electrotherapy system 100 according to a seventh implementation of the present disclosure. The implementation of the system 100 in FIG. 7 is directed to providing defibrillation and electrotherapy in a DDD configuration in which pacing and sensing is conducted on both the RA 14 and the RV 16 in a dual response mode.

In contrast to previously discussed implementations in which two separate leads were used to provide pacing and sensing of the RA 14 and the RV 16, the implementation of FIG. 7 includes a single RA/RV lead 216 screwed into the pericardium 12 of the heart 10 (or through the pericardium 12 into the underlying epicardium and myocardium) using a RA helical tip electrode 218. The RA/RV lead 216 further includes a defibrillator coil 208 proximal the helical tip electrode 218.

Sensing and pacing of the RA 14 and the RV 16 is provided by various electrodes disposed along the length of the RA/RV lead 216. More specifically, pacing and sensing of the RA 16 is provided by the RA helical tip electrode 218 and an RA ring electrode 220 disposed between the RA helical tip electrode 218 and the defibrillator coil 208. Pacing and sensing of the RV 16 is provided by a distal RV ring electrode 222 and a proximal RV ring electrode 224. As shown in FIG. 7, the proximal RV ring electrode 224 is disposed proximal the defibrillator coil 208 and the distal RV ring electrode 222 is disposed between the defibrillator coil 208 and the proximal RV ring electrode 222. The RA/RV lead 216 may be configured such that the helical tip electrode 218 acts as a cathode while the RA ring electrode 220 functions as a corresponding anode for pacing and sensing. Similarly, the RA/RV lead 216 may be configured such that the distal RV ring electrode 222 acts as a cathode while the proximal RV ring electrode 224 functions as a corresponding anode. Notably, however, the electrodes functioning as the anode and the cathode in either pair of electrodes may be reversed.

The RA/RV lead 216 is coupled to a pulse generator 102 such that the RA/RV lead 216 extends medially from the pulse generator 102 towards the heart 10. As illustrated in FIG. 7 and as discussed in further detail in FIG. 9, the defibrillator coil 208 of the RA/RV lead 216 may have an "s" or similar shape having one or more bends to increase contact area between the defibrillator coil 208 and the pericardium adjacent the RV 16. During operation, defibrillation may be provided by passing a current between the pulse generator 102 and the defibrillator coil 208.

Figure 9:
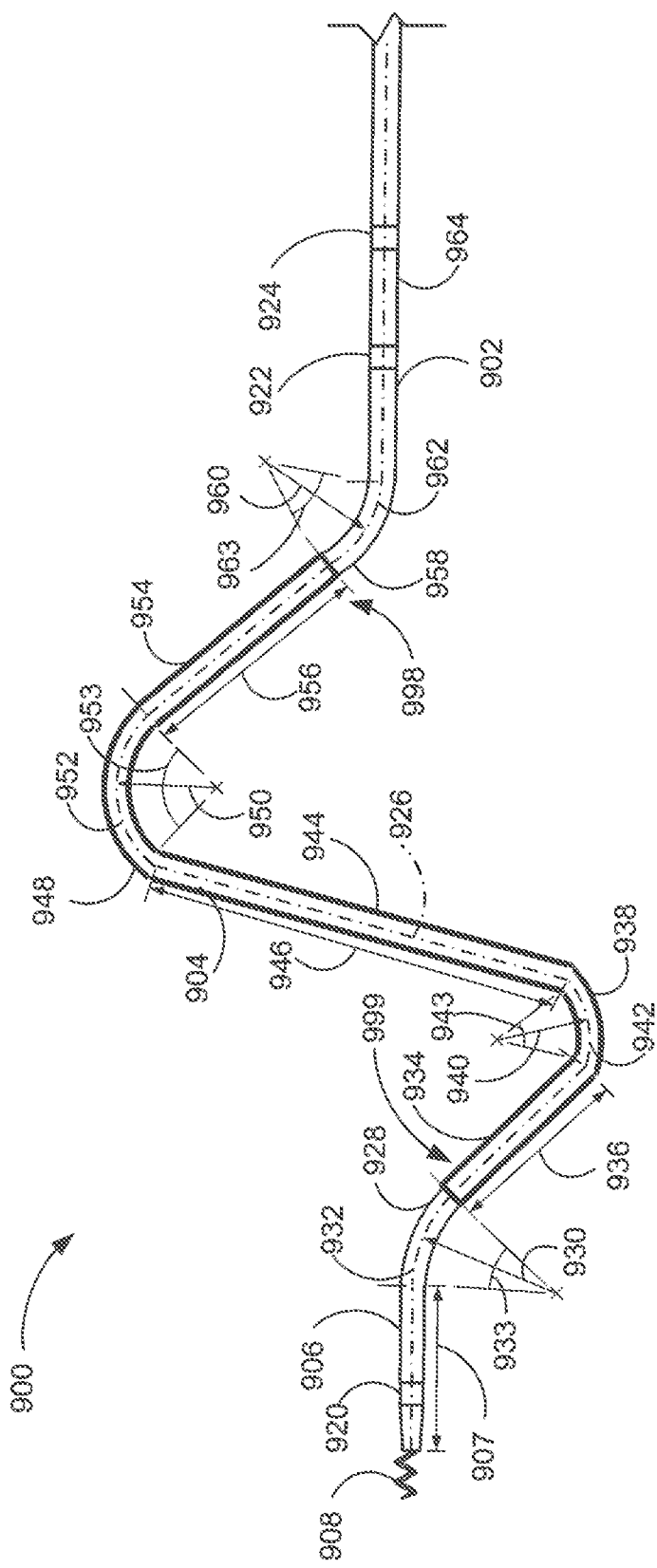
FIG. 9 is a plan view of an implantable medical lead for use in the electrotherapy system of FIG. 7.

FIGS. 8A-8B and 9 illustrate example leads for use in implementations of the present disclosure, including the implementations previously discussed in the context of FIGS. 1-7. Additional details regarding design and construction of leads that may be implemented in accordance with the present disclosure and, in particular, leads having both flexibility and improved torque transfer characteristics are also discussed in further detail in U.S. Pat. No. 9,211,406 to Bornzin et al., which is incorporated herein by reference.

FIG. 8A illustrates a first example lead 800 including a lead body 802, a defibrillator coil 804 disposed distal the lead body 802 and coupled to the lead body 802, a distal lead segment 806 coupled to and distally disposed from the defibrillator coil 804, and a helical tip electrode 808 disposed on the distal end of the lead 800.

During implantation, the helical tip electrode 808 is screwed into the pericardium by rotating the lead body 802 such that the helical tip electrode 808 engages adjacent cardiac tissue. The helical tip electrode 808 may then provide sensing and pacing in conjunction with a second electrode 810. In certain implementations, for example, the second electrode 810 may be a ring electrode 810 disposed along one of the lead body 802, the defibrillator coil 804, and the distal lead segment 806. In certain implementations, pacing and sensing may instead be conducted using other pairs of electrodes disposed along the lead 800 and the helical tip electrode 808 may instead function only as a fixation mechanism.

In certain implementations, the helical tip electrode 808 may extend from distal lead portion 806 a distance 814 from and including 1 millimeter (mm) to and including 3 mm with a pitch from and including 0.5 turns per mm to and including 2 turns per mm and a pitch diameter 812 from and including 1 mm to and including 3 mm. The helical tip electrode 808 may also be formed from a platinum iridium wire having a diameter from and including 0.25 mm to and including 0.4 mm. For example, in one implementation, the distance 814 from which the helical tip electrode 808 extends from the distal lead portion 806 is 3 mm from the distal lead segment 806 at a pitch of 1 turn per mm and a pitch diameter 812 of 1.5 mm, the helical tip electrode 808 being formed from platinum iridium wire having a diameter of 0.31 mm.

Portions of the lead 800, such as the lead body 802 and the distal lead segment 806, may be formed by a coiled cable braided or otherwise interwoven with a thermoplastic material or resin, such as polyethylene terephthalate (PET, also referred to as Dacron) such that the portions of the lead form a substantially cylindrical shape. By forming the lead 800 using a braided or similar interwoven construction, torsional stiffness of the lead 800 is increased relative to an unbraided construction. The resulting increased torsional stiffness improves torque transfer between the lead body 802 and the helical tip electrode 808 when a proximal end of the lead body 802 is rotated, thereby enabling fixation of the helical tip electrode 808 to cardiac tissue. In certain implementations, the torsional stiffness of leads according to this disclosure are from and including 0.11 to and including 0.5 in$^2$-oz/rad.

The defibrillator coil 804 may be formed from ribbon electrodes or flat ground platinum wire with layers of insulation disposed between adjacent turns of the defibrillator coil 804. For example, in certain implementations, the layers of insulation may be formed of a co-polymer of polyurethane and silicone, such as Optim™ or a similar co-polymer material.

The lead 800 may also be coated with a biocompatible coating that resists tissue adhesion. Such biocompatible coatings may include, without limitation, one of polytetrafluoroethylene (PTFE) and fluorinated ethylene propylene (FEP). Coating the lead 800 with such a biocompatible coating may, among other things, reduce friction and interference between the lead 800 and surrounding tissue when unscrewing the lead 800 and/or extracting the lead 800 using traction in the event the lead 800 is to be removed or repositioned.

The distal lead portion 806 and the defibrillator coil 804 may have predetermined lengths that may vary depending on the specific application of the lead 800. For example, dimensions of the lead 800 may be varied depending on whether the lead 800 is being used to provide pacing to the RA 14 or the RV 16, among other areas of the heart 10. When implemented to provide pacing and sensing of the RA 14, for example, the distal lead portion may have a length 818 from and including 1 mm to and including 15 mm and the defibrillator coil 804 may have a length 820 from and including 40 mm to and including 80 mm. The relatively short length of 818 is intended to reduce sensing of the far field RV depolarization signal while maintain an adequate RA sensing signal. In one implementation in which the lead 800 is used to provide pacing and sensing of the RA 14, the distal lead portion length 818 may be 5 mm and the defibrillator coil length 820 may be 60 mm. When implemented to provide pacing and sensing of the RV 16, the distal lead portion may have a length 818 from and including 2 mm to and including 15 mm and the defibrillator coil 804 may have a length 820 from and including 40 mm to and including 8 mm. In one implementation in which the lead 800 is used to provide pacing and sensing of the RV 16, the distal lead portion length 818 may be 5 mm and the defibrillator coil length 820 may be 60 mm.

FIG. 8B illustrates the example lead 800 of FIG. 8A with an alternative helical tip electrode 812. As shown in FIG. 8B, the alternative helical tip electrode 808 includes a proximal tip portion 826 having a first pitch diameter 822 that transitions into a distal tip portion 828 having a second pitch diameter 824 greater than the first pitch diameter 822. By extending the distal tip portion 828 in such a way, the distal tip portion 828 may more readily engage or "bite into" pericardial tissue when the lead 800 is advanced. In certain implementations, the proximal tip portion 826 may have a length from and including 1 mm to and including 3 mm and the first pitch diameter 822 may be from 1 mm to 2 mm and the distal tip portion 828 may have a length from and including 1 mm to and including 3 mm and the second pitch diameter 824 may be from 1 mm to 3 mm. For example, in one implementation, the proximal tip portion 826 may have a length of 3 mm and a first pitch diameter 822 of 1 mm and the distal tip portion 828 may have a length of 2 mm and the second pitch diameter 824 may be 3 mm.

FIG. 9 is a schematic illustration of a curvate lead 900, which may correspond to the RA/RV lead 216 of FIG. 7. The lead 900 includes a lead body 902, a defibrillator coil 904 disposed distal on the lead body 902 and coupled to the lead body 902, a distal lead segment 906 coupled to and distally disposed from the defibrillator coil 904, and a helical tip electrode 908 disposed on the distal end of the lead 900. The lead 900 further includes a tip ring electrode 920 disposed between the helical tip electrode 908 and the defibrillator coil 904 for providing pacing and sensing for a first area of cardiac tissue, such as the RA 14, and a pair of proximal ring electrodes 922, 924 disposed proximal the defibrillator coil 904 for providing pacing and sensing in a second area of cardiac tissue, such as the RV 16. In certain implementations, the curved shape of the curvate lead 900 may be imparted by using a thermoplastic polymer for the lead body 902 that is then heat treated to form the final lead shape. Alternatively, a thermosetting polymer, like silicone rubber, may be used to form the lead body 902. Such lead bodies may be held within a fixture that maintains the lead body 902 in the final curved shape during curing of the thermosetting polymer. The shape may be further reinforced by incorporating a heat treated s-shaped coil, such as a coil formed from MP35N or a similar alloy, into the lead body 902. Heat treatment of such a coil may be performed in an inert gas environment at high temperatures, such as temperatures from and including 1000 Fahrenheit to and including 1100 degrees Fahrenheit.

In certain implementations, the helical tip electrode 908 may extend from distal lead portion 906 from and including 1 mm to and including 4 mm with a pitch from and including 0.5 turns per mm to and including 2.5 turns per mm and a pitch diameter from and including 1 mm to and including 4 mm. The helical tip electrode 908 may also be formed from a platinum iridium wire having a diameter from and including 0.25 mm to and including 0.5 mm. For example, in one implementation, the helical tip electrode 908 extends 3 mm from the distal lead segment 906 at a pitch of 1 turn per mm and a pitch diameter of 1.5 mm and is formed from platinum iridium wire having a diameter of 0.31 mm.

The defibrillator coil 904 may have a diameter from and including 1 mm to and including 5 mm and have an overall length from and including 40 mm to and including 140 mm when straightened. For example, in one implementation, the defibrillator coil has a diameter of 2 mm and a length of 95 mm. The remaining length of the lead 900, including the lead body 902 and the distal lead segment 906 may have a diameter from and including 1 mm to and including 4 mm and, in certain implementations, may have a diameter of 1.5 mm.

The defibrillator coil 904 of the lead 900 may have sufficient stiffness such that, when implanted, the defibrillator coil 904 may be bent into an s- or similar shaped curve to increase contact between the defibrillator coil 904 and the pericardium adjacent the portion of the heart to which defibrillation is to be provided. As shown in FIG. 7, for example, the defibrillator coil 208 of the RV lead 216 is bent into an s-shape to increase contact between the defibrillator coil 208 and the RV 16. Referring back to FIG. 9, the s-bend of the defibrillator coil 904 may be bent such that a bend length of the defibrillator coil 904 (which may be defined as the distance between a proximal end 998 and a distal end 999 of the defibrillator coil 904) is a predetermined length based on the area of the pericardium to which the lead is to be fixed. For example, in implementations when the defibrillator coil 904 is to be adjacent the RV 14, the longitudinal length 926 may be approximately 54 mm.

In certain implementations, the curvate shape formed by the lead 900 may form an s-shape that conforms to a predetermined geometry as shown when not acted upon by an outside force. For purposes of the following discussion regarding the geometry of the lead 900, all dimensions are provided relative to a centerline 926 defined along the length of the lead 900.

As illustrated in FIG. 9, the centerline 926 of the curvate lead 900 follows an s-shaped path that transitions into substantially straight distal and proximal ends. More specifically, the lead 900 includes a distal lead portion 906 and a distal curved transition 928 proximal the distal lead portion 906 that transitions into a distal straight defibrillator section 934 of the defibrillator coil 904. The distal straight lead section 906 may have a length 907 from and including 4 mm to and including 15 mm. The distal curved transition 928 may have a radius of curvature 930 from and including 5 mm to and including 20 mm, an arc length 932 from and including 5 mm to and including 30 mm, and an angular extent 933 from and including 40 degrees to and including 85 degrees. The distal straight defibrillator section 934 may have a length 936 from and including 1 mm to and including 20 mm.

The distal straight defibrillator section 934 is coupled to a distal defibrillator curve 938 that transitions into a medial straight defibrillator section 944 proximal the distal defibrillator curve 938. The distal defibrillator curve 938 may have a radius of curvature 940 from and including 5 mm to and including 18 mm, an arc length 942 from and including 7 mm to and including 56 mm, and an angular extent 943 from and including 40 degrees to and including 180 degrees. The medial straight defibrillator section 944 may have a length 946 from and including 5 mm to and including 40 mm.

A proximal defibrillator curve 948 proximal the medial straight defibrillator section 944 transitions into a proximal straight defibrillator section 954. The proximal defibrillator curve 948 may have a radius of curvature 950 from and including 5 mm to and including 18 mm, an arc length 952 from and including 7 mm to and including 56 mm, and an angular extent 953 from and including 40 degrees to and including 180 degrees. The proximal straight defibrillator section 954 may have a length 956 from and including 1 mm to and including 25 mm.

Finally, the proximal straight defibrillator section 954 transitions to a proximal lead portion 964 by a proximal curved transition 958 disposed between the proximal straight defibrillator section 954 and the proximal curved transition 958. The proximal curved transition 958 may have a radius of curvature 960 from and including 5 mm to and including 20 mm, an arc length 962 from and including 4 mm to and including 30 mm, and an angular extent 963 from and including 40 degrees to and including 85 degrees. In certain implementations, the proximal lead portion may be from and including 200 mm to and including 700 mm in length.

Figure 10:
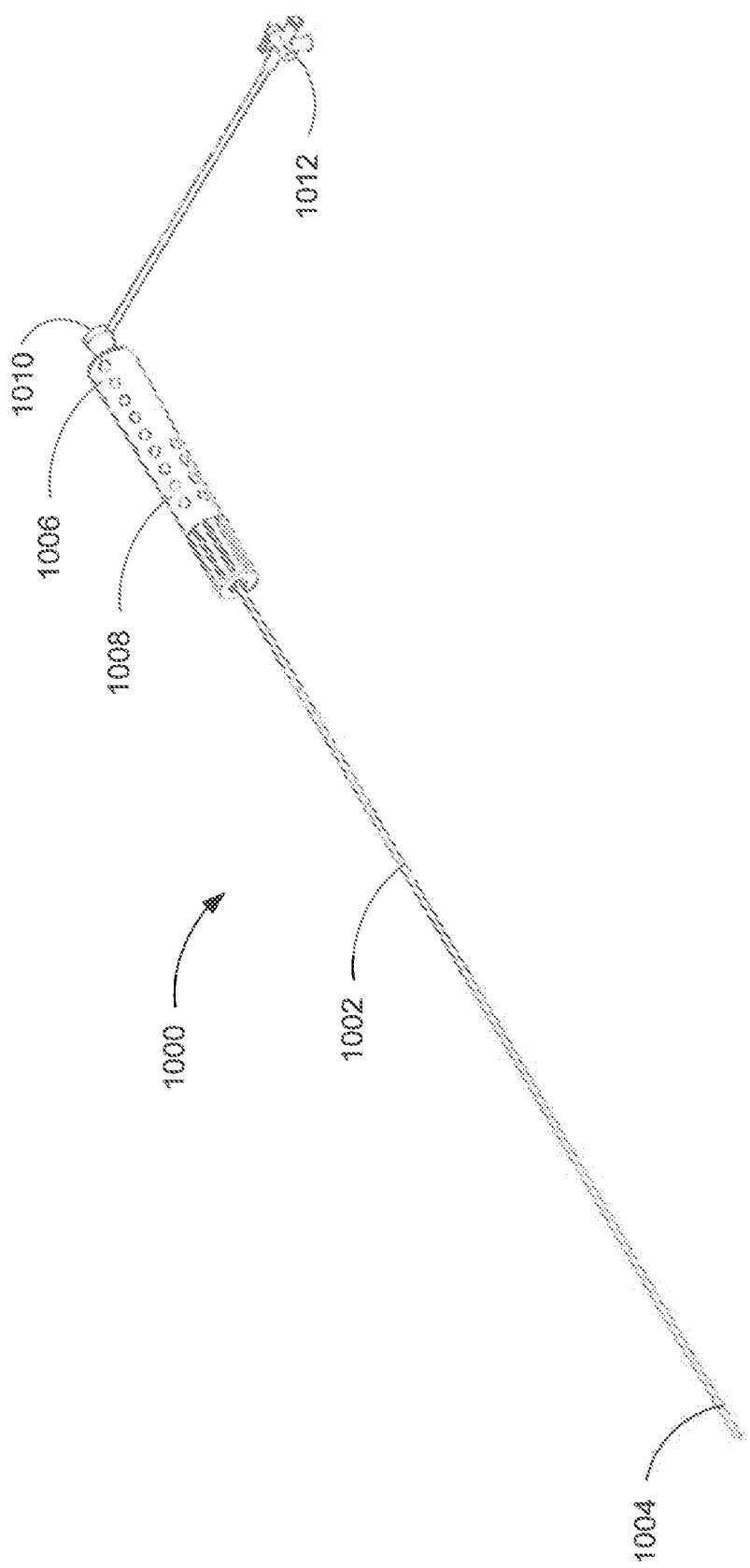
FIG. 10 is an isometric view of a first delivery system in accordance with this disclosure for delivery of an implantable medical lead.

FIG. 10 is a perspective view of a delivery system 1000 according to one embodiment of the present invention comprising a delivery catheter 1002 having a proximal portion 1004 and a distal portion 1006. The delivery catheter 1002 may be operably connected to a handle assembly 1008 which assists in guiding or steering the delivery catheter 1002 during procedures. The delivery system 1000 further includes a hub 1010 operably connected to an inner lumen (not shown) within the handle assembly 1008. Optionally, the catheter assembly 1002 further includes a valve 1012 operably connected to the hub 1010.

In certain implementations of the present disclosure, the delivery catheter 1002 of the delivery system 1000 may be steerable. For example, the catheter assembly may include a steering mechanism including one or more pull wires that, when pulled by actuation of the steering mechanism, cause the delivery catheter 1002 to bend and redirect the distal portion 1004 of the delivery catheter 1002. Examples of such delivery catheters include the Agilis™ line of steerable catheters and introducers available from Abbott (formerly St. Jude Medical).

In one example of a lead implantation process, the clinician first gains access to the mediastinal space, such as by using a sub-xiphoid stick. The delivery catheter 1002 is then advanced within the mediastinal space until the delivery catheter 1002 is disposed near a lead fixation location of the pericardium. Once in position, a sheath 1014 (shown in FIG. 11) is inserted through the lumen followed by a lead 1016 (shown in FIG. 11). Fluoroscopy may be used to further position the delivery catheter 1002, sheath 1014, and lead 1016 adjacent the fixation location. The lead 1016 may then be advanced, such as by rotation of the lead 1016, to cause a helical tip electrode 1018 (shown in FIG. 11) of the lead 1016 to protrude from the sheath 1014 and screw into the pericardium of the heart. In certain instances, the helical tip electrode 1018 may be further screwed in such that the helical tip electrode 1018 also engages the epicardium and myocardium.

Figure 11:
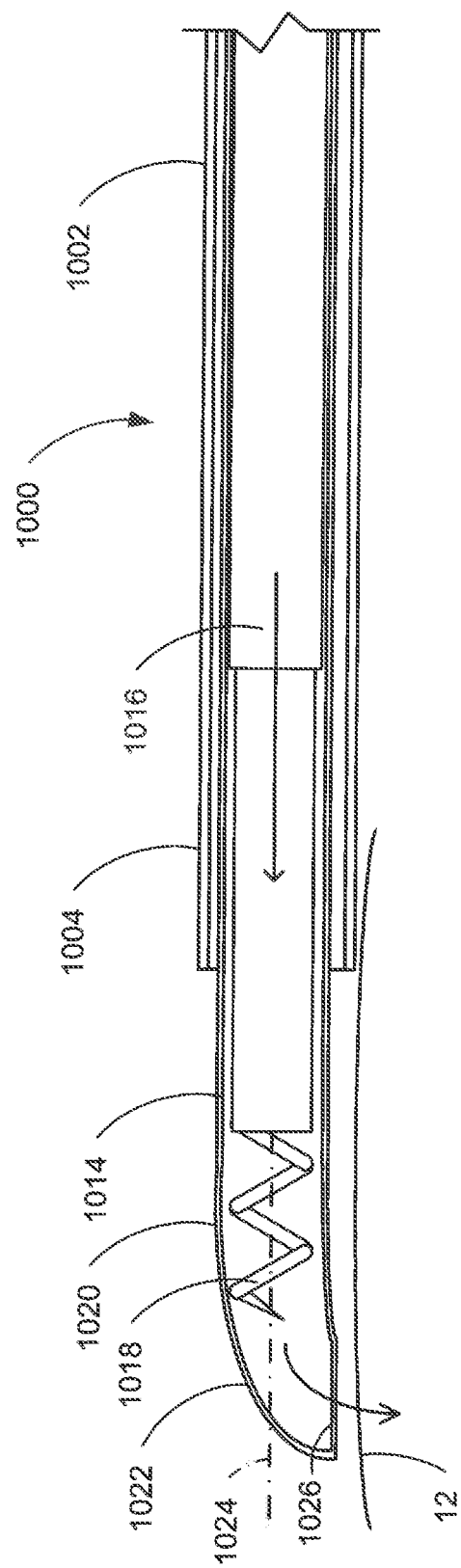
FIG. 11 is a cross-sectional view of a distal portion of the first delivery system.

FIG. 11 is a cross-sectional view of a distal end of the delivery system 1000 during a lead implantation process. The delivery system 1000 includes the delivery catheter 1002 into which the sheath 1014 is disposed such that the sheath 1014 extends beyond the distal end 1004 of the delivery catheter 1002. As show in FIG. 11, the sheath 1014 is shaped to receive the lead 1016, which may correspond to the leads previously described in FIGS. 8A-C and 9, and to deliver the lead 1016 at an angle towards the pericardium 12.

In certain implementations, the sheath 1014 may include a distal sheath tip 1020 shaped to direct the helical tip electrode 1018 of the lead 1016 as the lead 1016 is inserted into the sheath 1014. For example, the distal sheath tip 1020 of FIG. 11 has a curved wall 1022 that directs the helical tip electrode 1018 of the lead 1016 away from a longitudinal axis 1024 defined by the sheath 1014 and towards a portion of the pericardium 12. The curved wall 1022 may be reinforced by, among other things, increasing the wall thickness in the area of the curved wall 1022 or forming or otherwise disposing a hardened insert into the curved wall 1022. The sheath 1014 may further define a wall 1026 adjacent the curved wall 1022 through which the helical tip electrode 1018 is directed by the curved wall 1022. To facilitate direction of the helical tip electrode 1018, the wall 1026 may include a seam, score, or similar feature extending along the wall 1026 and adapted to split in response to the helical tip electrode 1018 contacting or being screwed through the wall 1026.

The sheath 1014 may be formed of a biocompatible material such as, without limitation, Pebax tubing and may have a wall thickness from and including 0.2 mm to and including 0.5 mm. The curved wall 1022 may have a radius of curvature from and including 5 mm to and including 30 mm, an arc length from and including 2 mm to and including 8 mm, and an angular extent from and including 45 degrees to and including 90 degrees such that the sheath 1014 delivers the helical tip electrode at an angle from and including 35 degrees to and including 90 degrees relative to the longitudinal axis 1024. For example, in one implementation, the sheath 1014 is formed from Pebax, has a wall thickness of 0.26 mm with a curved wall 1022 having a radius of curvature of 15 mm, an arc length of 6 mm, and an angular extent of 50 degrees.

Figure 12A:
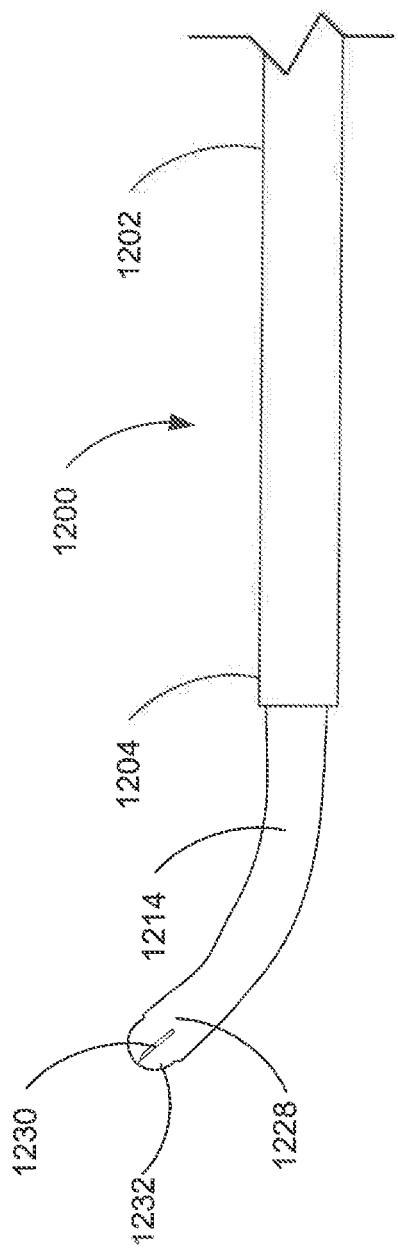
FIGS. 12A-12B are plan views of a distal portion of a second delivery system in accordance with the present disclosure.
Figure 12B:
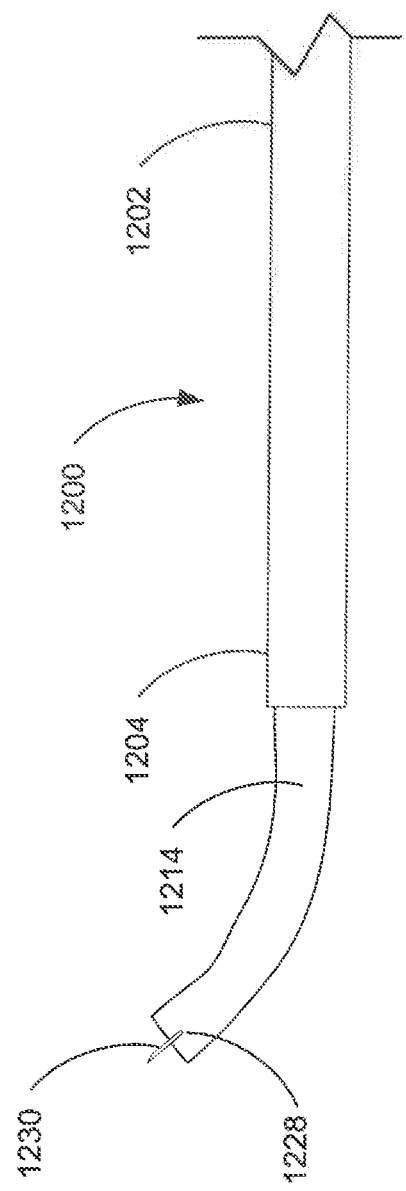

FIGS. 12A-12B are diagrammatic depictions of another delivery system 1200 in accordance with the present disclosure. The delivery system 1200 includes a delivery catheter 1202 into which a sheath 1214 is disposed such that the sheath 1214 extends beyond a distal end 1204 of the delivery catheter 1202. The sheath 1214 is generally shaped to receive a lead, which may correspond to the leads previously described in FIGS. 8A-C and 9. The sheath 1214 may include a curved distal end 1228 including a fixation tine 1230.

The sheath 1214 may be curved such that a lead inserted through the sheath 1214, and more particularly a helical tip electrode of the lead, is delivered to an implantation site at a predetermined angle. The angle of delivery of the helical tip electrode may further be controlled by directing the distal end of the delivery catheter 1202.

The distal end 1228 of the sheath 1214 may include one or more fixation tines, such as the fixation tine 1230, to engage the pericardium during fixation of the lead. In certain implementations, the fixation tine 1230 may extend from the distal end 1228 of the sheath 1214 from and including 0.25 mm to and including 1 mm and may have a diameter from and including 1 mm to and including 4 mm.

During the lead implantation procedure, the delivery system 1200 may be inserted into the mediastinum adjacent the heart such that the fixation tine 1230 engages an area of the pericardium adjacent the intended fixation site of the lead. The lead may be delivered within the sheath 1214 as the sheath 1214 and delivery catheter 1202 are inserted adjacent the heart or, in certain implementations, the lead may be inserted into the sheath 1214 after positioning of the sheath 1214 and fixation of the sheath 1214 using the fixation tine 1230.

During insertion of the sheath 1214, a distal tip 1232 of the sheath 1214 may be expanded by insertion of an obturator or similar device into the sheath 1214 such that the distal tip 1232 extends beyond the fixation tine 1230. In such a configuration, which is illustrated in FIG. 12A, the expanded distal tip 1232 and underlying obturator prevent engagement of the fixation tine 1230 with other tissue during insertion. When the sheath 1214 is near its final location, the obturator may be removed, as illustrated in FIG. 12B, such that the distal tip 1232 is no longer supported. By doing so, the fixation tine 1230 may be exposed and subsequently fixed to the pericardium adjacent the intended fixation site for the lead.

Once the sheath 1214 is positioned adjacent the intended fixation site of the lead, the lead may be inserted into the sheath 1214 and made to abut the distal end 1232 of the sheath 1214. The lead may then be rotated such that the helical tip electrode of the lead splits the distal end 1232 and exits the sheath 1214. As the lead is further rotated, the helical tip electrode engages and screws into the pericardium, fixing the lead. After engagement of the helical tip electrode, the fixation tine 1230 may be disengaged from the pericardium and each of the sheath 1214 and the delivery catheter 1202 may be removed from the mediastinum by sliding over the lead.

Figure 13C:
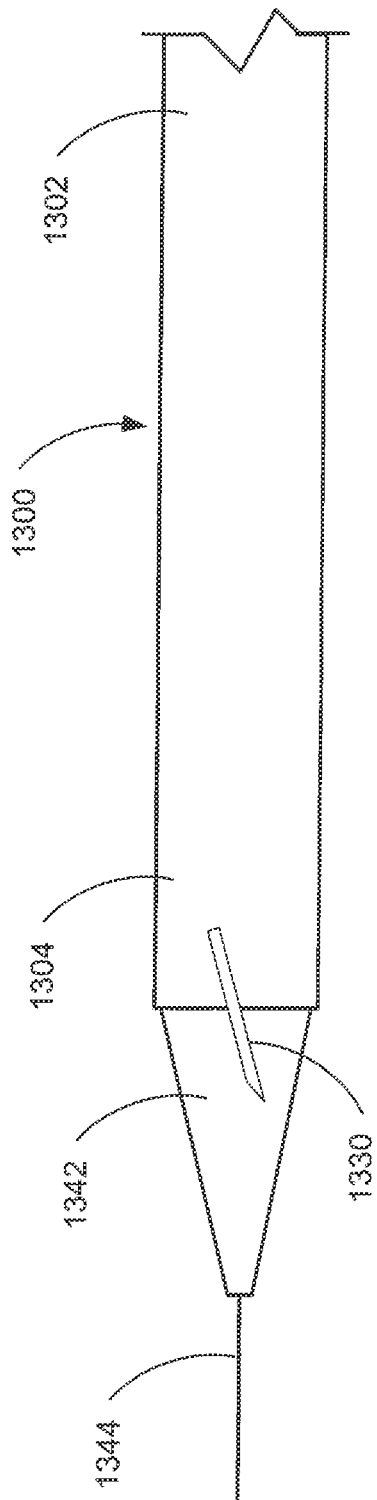

FIGS. 13A-13D graphically depict an alternative delivery system 1300 in accordance with the present disclosure. Similar to the delivery system 1200 illustrated in FIGS. 12A-12B, the delivery system 1300 includes a delivery catheter 1302 into which a sheath 1314 is disposed such that the sheath 1314 extends beyond the distal end of the delivery catheter 1302, as shown in FIG. 13B. The sheath 1314 may be generally shaped to receive a lead, which may correspond to the leads previously described in FIGS. 8A-C and 9.

The delivery catheter 1302 of the delivery system 1300 may include one or more fixation tines 1330, 1331 disposed on a distal end 1304 of the delivery catheter 1302. During implantation, the delivery catheter 1302 may be inserted into the mediastinum adjacent the fixation location of the lead and fixed to the pericardium using the fixation tines 1330, 1331. Once fixed, the sheath 1314 may then be inserted into the delivery catheter 1302 (as shown in FIG. 13B) to direct the lead to the fixation location. The sheath 1314 and the lead may be inserted into the delivery catheter 1302 together or consecutively. After placement of the lead adjacent the fixation site, the lead may be rotated to advance a helical tip electrode of the lead through the sheath 1314 and into the pericardium.

During fixation of the helical tip electrode to the pericardium, the fixation tines 1330, 1331 anchor the adjacent tissue such that the tissue does not twist or otherwise wrap around the helical tip electrode. In certain implementations, the fixation tines 1330, 1331 may extend from the delivery catheter 1302 at an angle opposite the angle of rotation required to fix the helical tip electrode to the pericardium. For example, in implementations in which fixation of the lead is achieved by clockwise rotation of the lead, the tine may extend in a counter-clockwise direction at an angle θ relative to a longitudinal axis 1340 of the delivery catheter 1302. The angle θ may be from and including 30 degrees to and including 75 degrees relative to the longitudinal axis 1340. In implementations including angled fixation tines, engagement of the fixation tines may include rotating the delivery catheter 1302 to cause the angled fixation tines to engage the pericardium. In delivery systems according to this disclosure in which the sheath includes fixation tines, such as the delivery system 1200 illustrated in FIGS. 12A-12B, the fixation tines coupled to the sheath may also be angled as described above.

Figure 13D:
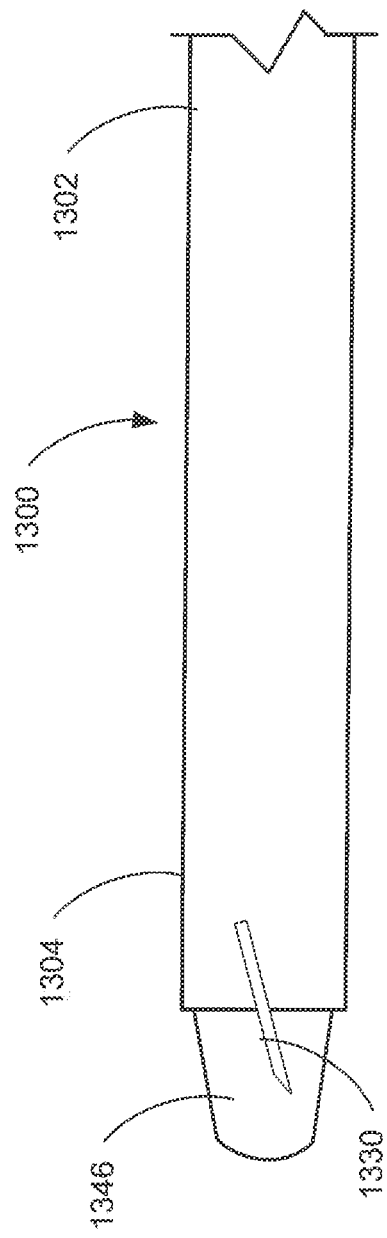

As illustrated in FIGS. 13C and 13D, the delivery catheter 1302 may be fitted with various tips for facilitating different functionality. For example, as shown in FIG. 13C, a dilator 1342 may be coupled to the distal end 1304 of the delivery catheter 1302 to facilitate insertion of the delivery catheter 1302 into the mediastinum using the Seldinger technique. More specifically, a Touhy needle (not shown) is used to gain access to the mediastinum through a subxiphoid or fifth intercostal left parasternal stick. A guidewire 1344, which may be a 0.032" or a 0.038" guidewire in certain implementations, is then advanced into the mediastinum through a needle. The needle is then removed by pulling the needle over the guidewire 1344 that is left in place in the mediastinum. Next, the delivery catheter 1302 with the dilator 1342 inserted therethrough is advanced over the guidewire 1344 and pushed through the skin and muscle into the mediastinum. The dilator 1342 acts like a wedge to blunt dissect a hole large enough to accommodate the delivery catheter 1302. Once the dilator 1342 and the delivery catheter 1302 are advanced into the mediastinum, the dilator 1342 and the guidewire 1344 can be removed, leaving the delivery catheter 1302 in place in the mediastinum.

FIG. 13D illustrates another implementation of the delivery catheter 1302 in which an obturator 1346 is disposed on the distal end 1304 $f$ the delivery catheter 1302. For example, after removing the guide wire 1344 during execution of the Seldinger technique, the obturator 1346 may be advanced into the delivery catheter 1302 to provide a smooth blunt tip that protects the mediastinal tissue from injury as the delivery catheter is steered under fluoroscopy to the target implant site. The obturator 1346 may also be shaped to protect the surrounding mediastinal tissue from being engaged and damaged by the distal tip 1304 of the delivery catheter 1302 and, in particular, by snagging of the fixation tines 1330, 1331. Once the delivery catheter 1302 is properly positioned, the obturator 1346 may be pulled back such that the fixation tines 1330, 1331 can engage the pericardium and stabilize the pericardium as the lead is screwed into or through the pericardium.

While the term catheter is employed herein to describe a tubular device for implantable lead delivery, the term catheter is intended to also encompass other types of tubular bodies adapted for delivery of implantable medical leads, including sheaths. Thus, the term catheter should be interpreted as including both catheters and sheaths, and other tubular lead delivery devices and should not be otherwise limited in scope.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A delivery system for delivering an implantable medical lead to an implantation site on a pericardium of a patient heart, the implantable medical lead including a helical tip electrode disposed on a distal end of the medical lead, the delivery system comprising:
    a delivery catheter having a proximal catheter end and a distal catheter end opposite the proximal catheter end, the delivery catheter defining an inner lumen, the delivery catheter configured to be advanced to the implantation site on the pericardium;
    a lead receiving sheath within and extending along the inner lumen, the lead receiving sheath having a proximal sheath end and a distal sheath end opposite the proximal sheath end, the distal sheath end configured to be located at the implantation site on the pericardium; and
    a fixation tine extending from one of the distal catheter end and the distal sheath end, the fixation tine located relative to the distal sheath end and shaped to engage the pericardium to dispose the distal sheath end adjacent to the implantation site.

2. The delivery system of claim 1, wherein the delivery catheter is a steerable catheter.

3. The delivery system of claim 1, wherein the lead receiving sheath defines a sheath longitudinal axis and the distal sheath end comprises a sheath tip shaped to bias the medical lead away from the sheath longitudinal axis when the medical lead is inserted into the lead receiving sheath.

4. The delivery system of claim 3, wherein the sheath tip comprises a reinforced curved surface that biases the medical lead away from the sheath longitudinal axis.

5. The delivery system of claim 3, wherein the sheath tip comprises a tip wall, the tip wall defining a score adapted to split in response to the helical tip electrode of the medical lead at least one of contacting and being screwed through the tip wall.

6. The delivery system of claim 1, wherein the lead receiving sheath comprises a curved distal portion proximal the distal sheath end and proximal the fixation tine, the curved distal portion configured to direct the helical tip electrode to the implantation site on the pericardium.

7. The delivery system of claim 1, wherein the lead receiving sheath is constructed of at least one of Pebax, polyurethane, polyethylene and has a wall thickness from and including 0.2 mm to and including 0.5 mm.

8. The delivery system of claim 7, wherein the lead receiving sheath is constructed of Pebax and has a wall thickness of 0.26 mm.

9. The delivery system of claim 1, wherein the fixation tine is one of a plurality of fixation tines distributed about the one of the distal catheter end and the distal sheath end.

10. The delivery system of claim 1, wherein the fixation tine extends from and including 0.25 mm to and including 1 mm from the one of the distal catheter end and the distal sheath end and at an angle from and including zero degrees to and including 75 degrees relative to a longitudinal axis of the one of the distal catheter end and the distal sheath end.

11. The delivery system of claim 1, wherein the fixation tine is one of a plurality of tines distributed about the one of the distal catheter end and the distal sheath end, each of the plurality of tines extending 0.4 mm from the one of the distal catheter end and the distal sheath end at an angle of 45 degrees relative to a longitudinal axis of the one of the distal catheter end and the distal sheath end.

12. The delivery system of claim 1, wherein the one of the distal catheter end and the distal sheath end further comprises an obturator extending past a distal end of the fixation tine.

13. The delivery system of claim 1, wherein the distal sheath end comprises a sheath tip configured to be located at the implantation site on the pericardium.

14. The delivery system of claim 13, further comprising the implantable medical lead, the helical tip electrode disposed on the distal end of the medical lead configured to pass through the sheath tip.

15. A delivery system for delivering an implantable medical lead to an implantation site on a pericardium of a patient heart, the implantable medical lead including a helical tip electrode disposed on a distal end of the medical lead, the delivery system comprising:
- a delivery catheter having a proximal catheter end and a distal catheter end opposite the proximal catheter end, the delivery catheter defining an inner lumen;
- a lead receiving sheath within and extending along the inner lumen, the lead receiving sheath having a proximal sheath end and a distal sheath end opposite the proximal sheath end; and
- a fixation tine extending from one of the distal catheter end and the distal sheath end, the fixation tine located relative to the distal sheath end and shaped to engage the pericardium to dispose the distal sheath end adjacent the implantation site,
- wherein the lead receiving sheath defines a sheath longitudinal axis and the distal sheath end comprises a sheath tip shaped to bias the medical lead away from the sheath longitudinal axis when the medical lead is inserted into the lead receiving sheath,
- wherein the sheath tip comprises a tip wall, the tip wall defining a score adapted to split in response to the helical tip electrode of the medical lead at least one of contacting and being screwed through the tip wall.

16. A delivery system for delivering an implantable medical lead to an implantation site on a pericardium of a patient heart, the implantable medical lead including a helical tip electrode disposed on a distal end of the medical lead, the delivery system comprising:
- a delivery catheter having a proximal catheter end and a distal catheter end opposite the proximal catheter end, the delivery catheter defining an inner lumen;
- a lead receiving sheath within and extending along the inner lumen, the lead receiving sheath having a proximal sheath end and a distal sheath end opposite the proximal sheath end; and
- a fixation tine extending from one of the distal catheter end and the distal sheath end, the fixation tine located relative to the distal sheath end and shaped to engage the pericardium to dispose the distal sheath end adjacent the implantation site,
- wherein the fixation tine is one of a plurality of tines distributed about the one of the distal catheter end and the distal sheath end, each of the plurality of multiple tines extending 0.4 mm from the one of the distal catheter end and the distal sheath end at an angle of 45 degrees relative to a longitudinal axis of the one of the distal catheter end and the distal sheath end.

* * * * *